United States Patent
Stone et al.

(10) Patent No.: US 9,763,656 B2
(45) Date of Patent: Sep. 19, 2017

(54) METHOD AND APPARATUS FOR SOFT TISSUE FIXATION

(71) Applicant: Biomet Sports Medicine, LLC, Warsaw, IN (US)

(72) Inventors: Kevin T. Stone, Winona Lake, IN (US); Gregory J. Denham, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 516 days.

(21) Appl. No.: 14/182,038

(22) Filed: Feb. 17, 2014

(65) Prior Publication Data
US 2014/0163613 A1    Jun. 12, 2014

Related U.S. Application Data

(60) Division of application No. 13/098,927, filed on May 2, 2011, now Pat. No. 8,652,171, which is a
(Continued)

(51) Int. Cl.
A61B 17/04 (2006.01)
A61B 17/06 (2006.01)
A61B 17/00 (2006.01)

(52) U.S. Cl.
CPC .... *A61B 17/0401* (2013.01); *A61B 17/06166* (2013.01); *A61B 17/0487* (2013.01);
(Continued)

(58) Field of Classification Search
CPC .......... A61B 17/0401; A61B 17/06166; A61B 2017/00406; A61B 2017/0406; A61B 2017/0417
See application file for complete search history.

(56) References Cited

U.S. PATENT DOCUMENTS 65,499 A    6/1867  Miller
126,366 A   4/1872  Wills
(Continued)

FOREIGN PATENT DOCUMENTS

AU    4957264     3/1966
AU     440266    10/1967
(Continued)

OTHER PUBLICATIONS

US 6,238,418, 05/2001, Schwartz et al. (withdrawn)
(Continued)

*Primary Examiner* — Dianne Dornbusch
(74) *Attorney, Agent, or Firm* — Schwegman Lundberg & Woessner, P.A.

(57) ABSTRACT

A tissue fixation apparatus can include a flexible construct and an elongated locking member. The flexible construct can include at least two adjustable loops and tensioning members. The two adjustable loops can be configured to pass through the first tissue, and to be spaced apart along an outer surface of the first tissue in a first direction. The tensioning members can extend from the two adjustable loops, and can be configured to reduce the two adjustable loops from a first size to a second size. The flexible construct can be attached to the second tissue by an anchor. The locking member can be configured to be received within the two adjustable loops at the first size, and to engage the two adjustable loops at the second size.

20 Claims, 6 Drawing Sheets

Related U.S. Application Data continuation-in-part of application No. 12/196,398, filed on Aug. 22, 2008, now Pat. No. 7,959,650, which is a continuation-in-part of application No. 11/541,506, filed on Sep. 29, 2006, now Pat. No. 7,601,165, and a continuation-in-part of application No. 11/935,681, filed on Nov. 6, 2007, now Pat. No. 7,905,903, and a continuation-in-part of application No. 11/784,821, filed on Apr. 10, 2007, now Pat. No. 9,017,381, application No. 14/182,038, which is a division of application No. 13/098,927, filed on May 2, 2011, now Pat. No. 8,652,171, which is a continuation-in-part of application No. 12/938,902, filed on Nov. 3, 2010, now Pat. No. 8,597,327, which is a continuation-in-part of application No. 12/915,962, filed on Oct. 29, 2010, now Pat. No. 8,562,647, which is a continuation-in-part of application No. 12/719,337, filed on Mar. 8, 2010, now Pat. No. 9,078,644, which is a continuation-in-part of application No. 12/489,168, filed on Jun. 22, 2009, now Pat. No. 8,361,113, which is a continuation-in-part of application No. 12/474,802, filed on May 29, 2009, now Pat. No. 8,088,130, which is a continuation-in-part of application No. 12/196,405, filed on Aug. 22, 2008, now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836, and a continuation-in-part of application No. 11/541,506, filed on Sep. 29, 2006, now Pat. No. 7,601,165, application No. 14/182,038, which is a division of application No. 13/098,927, filed on May 2, 2011, now Pat. No. 8,652,171, which is a continuation-in-part of application No. 12/788,978, filed on May 27, 2010, now Pat. No. 8,801,783, application No. 14/182,038, which is a division of application No. 13/098,927, filed on May 2, 2011, now Pat. No. 8,652,171, which is a continuation-in-part of application No. 12/702,067, filed on Feb. 8, 2010, now Pat. No. 8,672,982, which is a continuation of application No. 11/541,505, filed on Sep. 29, 2006, now Pat. No. 7,658,751, application No. 14/182,038, which is a division of application No. 13/098,927, filed on May 2, 2011, now Pat. No. 8,652,171, which is a continuation-in-part of application No. 12/570,854, filed on Sep. 30, 2009, now Pat. No. 8,303,604, which is a continuation-in-part of application No. 12/489,181, filed on Jun. 22, 2009, now Pat. No. 8,298,262, and a continuation-in-part of application No. 12/014,399, filed on Jan. 15, 2008, now Pat. No. 7,909,851, which is a continuation-in-part of application No. 11/347,661, filed on Feb. 3, 2006, now Pat. No. 7,749,250, said application No. 12/570,854 is a continuation-in-part of application No. 12/014,340, filed on Jan. 15, 2008, now Pat. No. 7,905,904.

(52) U.S. Cl.
CPC ............ *A61B 2017/00336* (2013.01); *A61B 2017/00858* (2013.01); *A61B 2017/044* (2013.01); *A61B 2017/0406* (2013.01); *A61B 2017/0417* (2013.01); *A61B 2017/0477* (2013.01); *A61B 2017/06185* (2013.01)

(56) References Cited

U.S. PATENT DOCUMENTS

| | | |
|---|---|---|
| 233,475 A | 10/1880 | Cook et al. |
| 261,501 A | 7/1882 | Vandermark |
| 268,407 A | 12/1882 | Hughes |
| 330,087 A | 11/1885 | Binns |
| 394,739 A | 12/1888 | Toulmin |
| 401,677 A | 4/1889 | Autenrieth |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| 2,397,216 A | 3/1946 | Stellin |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 2,947,504 A | 8/1960 | Ruhlman |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,081,781 A | 3/1963 | Stermer |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Himmelstein et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,545,008 A | 12/1970 | Bader, Jr. |
| 3,547,389 A | 12/1970 | Mitchell |

(56) References Cited

U.S. PATENT DOCUMENTS

| | | |
|---|---|---|
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,650,274 A | 3/1972 | Edwards et al. |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,084,478 A | 4/1978 | Simmons |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,146,022 A | 3/1979 | Johnson et al. |
| 4,149,277 A | 4/1979 | Bokros |
| 4,157,714 A | 6/1979 | Foltz et al. |
| 4,158,250 A | 6/1979 | Ringwald |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,490 A | 6/1981 | Bivins |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,489,464 A | 12/1984 | Massari et al. |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,587,963 A | 5/1986 | Leibinger et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |

(56) References Cited

U.S. PATENT DOCUMENTS

| | | |
|---|---|---|
| 4,636,121 A | 1/1987 | Miller |
| 4,640,271 A | 2/1987 | Lower |
| 4,641,652 A | 2/1987 | Hutterer et al. |
| 4,649,916 A | 3/1987 | Frimberger |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,736,746 A | 4/1988 | Anderson |
| 4,738,255 A | 4/1988 | Goble et al. |
| 4,739,751 A | 4/1988 | Sapega et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,751,922 A | 6/1988 | Dipietropolo |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane |
| 4,787,882 A | 11/1988 | Claren et al. |
| 4,790,297 A | 12/1988 | Luque et al. |
| 4,790,850 A | 12/1988 | Dunn et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,603 A | 8/1989 | Clemow et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,873,976 A | 10/1989 | Schreiber |
| 4,884,572 A | 12/1989 | Bays et al. |
| 4,887,601 A | 12/1989 | Richards |
| 4,889,110 A | 12/1989 | Galline et al. |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,020,713 A | 6/1991 | Kunreuther |
| 5,026,398 A | 6/1991 | May et al. |
| 5,030,224 A | 7/1991 | Wright et al. |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,071,420 A | 12/1991 | Paulos et al. |
| 5,074,874 A | 12/1991 | Yoon et al. |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,866 A | 3/1992 | Breard et al. |
| 5,098,433 A | 3/1992 | Freedland |
| 5,098,435 A | 3/1992 | Stednitz et al. |
| 5,100,415 A | 3/1992 | Hayhurst |
| 5,100,417 A | 3/1992 | Cerier et al. |
| 5,108,433 A | 4/1992 | May et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |

(56) References Cited

U.S. PATENT DOCUMENTS

| | | |
|---|---|---|
| 5,163,960 A | 11/1992 | Bonutti |
| D331,626 S | 12/1992 | Hayhurst et al. |
| 5,169,400 A | 12/1992 | Muhling et al. |
| 5,171,274 A | 12/1992 | Fluckiger et al. |
| 5,176,682 A | 1/1993 | Chow |
| 5,178,629 A | 1/1993 | Kammerer |
| 5,183,458 A | 2/1993 | Marx |
| 5,190,545 A | 3/1993 | Corsi et al. |
| 5,192,282 A | 3/1993 | Draenert et al. |
| 5,197,987 A | 3/1993 | Koch et al. |
| 5,199,135 A | 4/1993 | Gold |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |
| 5,314,429 A | 5/1994 | Goble |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,350,380 A | 9/1994 | Goble et al. |
| RE34,762 E | 10/1994 | Goble et al. |
| 5,354,292 A | 10/1994 | Braeuer et al. |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,646 A | 12/1994 | Reese et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,395,374 A | 3/1995 | Miller et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,411,550 A | 5/1995 | Herweck et al. |
| 5,415,658 A | 5/1995 | Kilpela et al. |
| 5,417,690 A | 5/1995 | Sennett et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,824 A | 6/1995 | Akerfeldt et al. |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,721 A | 10/1995 | Legrand |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |

(56) References Cited

U.S. PATENT DOCUMENTS

| | | |
|---|---|---|
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,489,210 A | 2/1996 | Hanosh |
| 5,490,750 A | 2/1996 | Gundy |
| 5,495,974 A | 3/1996 | Deschenes et al. |
| 5,496,331 A | 3/1996 | Xu et al. |
| 5,496,348 A | 3/1996 | Bonutti |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,569,306 A | 10/1996 | Thal |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,547 A | 11/1996 | LeVeen et al. |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,607,430 A | 3/1997 | Bailey |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,960 A | 7/1997 | Pavletic |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada et al. |
| 5,690,655 A | 11/1997 | Hart et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,709,708 A | 1/1998 | Thal |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,715,578 A | 2/1998 | Knudson |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,725,529 A | 3/1998 | Nicholson et al. |
| 5,725,549 A | 3/1998 | Lam |
| 5,725,556 A | 3/1998 | Moser et al. |
| 5,725,557 A | 3/1998 | Gatturna et al. |
| 5,725,581 A | 3/1998 | Brånemark |
| 5,725,582 A | 3/1998 | Bevan et al. |

(56) References Cited

U.S. PATENT DOCUMENTS

| | | |
|---|---|---|
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor et al. |
| 5,800,543 A | 9/1998 | Mcleod et al. |
| 5,810,824 A | 9/1998 | Chan |
| 5,810,848 A | 9/1998 | Hayhurst |
| 5,814,056 A | 9/1998 | Prosst et al. |
| 5,814,069 A | 9/1998 | Schulze et al. |
| 5,814,070 A | 9/1998 | Borzone et al. |
| 5,814,071 A | 9/1998 | Mcdevitt et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,824,066 A | 10/1998 | Gross |
| 5,830,234 A | 11/1998 | Wojciechowicz et al. |
| 5,836,955 A | 11/1998 | Buelna et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,973 A | 1/1999 | Michelson |
| 5,860,978 A | 1/1999 | McDevitt et al. |
| 5,868,740 A | 2/1999 | LeVeen et al. |
| 5,868,748 A | 2/1999 | Burke |
| 5,868,789 A | 2/1999 | Huebner |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,129 A | 8/1999 | Mcdevitt et al. |
| 5,935,133 A | 8/1999 | Wagner et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,520 A | 10/1999 | Beck, Jr. et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,548 A | 11/1999 | Evans et al. |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,007,538 A | 12/1999 | Levin |
| 6,007,567 A | 12/1999 | Bonutti |
| 6,010,525 A | 1/2000 | Bonutti et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,042,609 A | 3/2000 | Giordano et al. |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |

(56) References Cited

U.S. PATENT DOCUMENTS

| | | |
|---|---|---|
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | McKernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,110,207 A | 8/2000 | Eichhorn et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,136,010 A | 10/2000 | Modesitt et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,174,324 B1 | 1/2001 | Egan et al. |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,303,158 B1 | 10/2001 | Odgaard et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,334,064 B1 | 12/2001 | Fiddian-green |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,111 B1 | 5/2002 | Barber |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,425,924 B1 | 7/2002 | Rousseau |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-Young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |

(56) References Cited

U.S. PATENT DOCUMENTS

| | | |
|---|---|---|
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,514,274 B1 | 2/2003 | Boucher et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 * | 2/2003 | Hein .................. A61F 2/0811 606/232 |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,543,094 B2 | 4/2003 | D'Addario |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,167 B1 | 5/2003 | Bobechko et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,064 B1 | 8/2003 | Goble et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues |
| 6,626,919 B1 | 9/2003 | Swanstrom |
| 6,626,930 B1 | 9/2003 | Allen et al. |
| 6,629,977 B1 | 10/2003 | Wolf |
| 6,632,245 B2 | 10/2003 | Kim |
| 6,635,073 B2 | 10/2003 | Bonutti |
| 6,638,279 B2 | 10/2003 | Bonutti |
| 6,638,286 B1 | 10/2003 | Burbank et al. |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,211 B2 | 11/2003 | Magana |
| 6,645,227 B2 | 11/2003 | Fallin et al. |
| 6,648,903 B1 | 11/2003 | Pierson, III |
| 6,648,921 B2 | 11/2003 | Anderson et al. |
| 6,652,450 B2 | 11/2003 | Neisz et al. |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,669,707 B1 | 12/2003 | Swanstrom et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,712,859 B2 | 3/2004 | Rousseau |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,755,868 B2 | 6/2004 | Rousseau |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,793,595 B1 | 9/2004 | Monnet |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,243 B2 | 5/2005 | Culbert |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |

(56) References Cited

U.S. PATENT DOCUMENTS

| | | |
|---|---|---|
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,719 B2 | 2/2006 | Grafton |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,083,638 B2 | 8/2006 | Foerster |
| 7,087,064 B1 | 8/2006 | Hyde |
| 7,087,073 B2 | 8/2006 | Bonutti |
| 7,097,654 B2 | 8/2006 | Freedland |
| 7,101,395 B2 | 9/2006 | Tremulis et al. |
| 7,105,010 B2 | 9/2006 | Hart et al. |
| 7,112,221 B2 | 9/2006 | Harris |
| 7,118,578 B2 | 10/2006 | West, Jr. et al. |
| 7,118,583 B2 | 10/2006 | O'Quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B1 | 2/2007 | Andrews |
| 7,201,722 B2 | 4/2007 | Krueger |
| 7,207,993 B1 | 4/2007 | Baldwin et al. |
| 7,229,441 B2 | 6/2007 | Trieu et al. |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 | 10/2007 | Brown et al. |
| 7,285,124 B2 | 10/2007 | Foerster |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn et al. |
| 7,484,539 B1 | 2/2009 | Huang |
| 7,485,149 B1 | 2/2009 | White |
| 7,494,506 B2 | 2/2009 | Brulez et al. |
| D587,807 S | 3/2009 | Wolf et al. |
| 7,500,983 B1 | 3/2009 | Kaiser et al. |
| 7,513,910 B2 | 4/2009 | Buskirk et al. |
| 7,517,357 B2 | 4/2009 | Abrams et al. |
| 7,572,275 B2 | 8/2009 | Fallin et al. |
| 7,572,298 B2 | 8/2009 | Roller et al. |
| 7,578,825 B2 | 8/2009 | Huebner |
| 7,585,311 B2 | 9/2009 | Green et al. |
| 7,588,587 B2 | 9/2009 | Barbieri et al. |
| 7,591,823 B2 | 9/2009 | Tipirneni |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,691,112 B2 | 4/2010 | Chanduszko et al. |
| 7,695,493 B2 | 4/2010 | Saadat et al. |
| 7,695,503 B1 | 4/2010 | Kaiser et al. |
| 7,703,372 B1 | 4/2010 | Shakespeare |
| 7,713,285 B1 | 5/2010 | Stone et al. |
| 7,717,929 B2 | 5/2010 | Fallman |
| 7,731,732 B2 | 6/2010 | Ken |
| 7,736,364 B2 | 6/2010 | Stone |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,762,942 B2 | 7/2010 | Neisz et al. |
| 7,776,041 B1 | 8/2010 | Walters |
| 7,790,945 B1 | 9/2010 | Watson, Jr. |
| 7,803,173 B2 | 9/2010 | Burkhart et al. |
| 7,819,895 B2 | 10/2010 | Ginn et al. |
| 7,828,820 B2 | 11/2010 | Stone et al. |
| 7,828,850 B2 | 11/2010 | Cauthen, III et al. |
| 7,856,698 B2 | 12/2010 | Hays |
| 7,857,830 B2 | 12/2010 | Stone et al. |
| 7,867,252 B2 | 1/2011 | Criscuolo et al. |
| 7,867,264 B2 | 1/2011 | McDevitt et al. |
| 7,875,058 B2 | 1/2011 | Holmes, Jr. |
| 7,878,058 B2 | 2/2011 | Blendinger et al. |
| 7,887,586 B2 | 2/2011 | Linares |
| 7,896,907 B2 | 3/2011 | Mcdevitt et al. |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,951,198 B2 | 5/2011 | Sucec et al. |
| 7,955,388 B2 | 6/2011 | Jensen et al. |
| 7,959,650 B2 | 6/2011 | Kaiser et al. |
| 7,976,565 B1 | 7/2011 | Meridew |
| 7,981,140 B2 | 7/2011 | Burkhart |
| 7,998,203 B2 | 8/2011 | Blum |
| 8,062,334 B2 | 11/2011 | Green et al. |
| 8,075,574 B2 | 12/2011 | May et al. |
| 8,088,130 B2 | 1/2012 | Kaiser et al. |
| 8,109,867 B2 | 2/2012 | Rosenblatt |
| 8,114,127 B2 | 2/2012 | West, Jr. |
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,128,658 B2 | 3/2012 | Kaiser et al. |
| 8,137,354 B2 | 3/2012 | Stone |
| 8,137,382 B2 | 3/2012 | Denham et al. |
| 8,162,997 B2 | 4/2012 | Struhl |
| 8,167,906 B2 | 5/2012 | Cauldwell et al. |
| 8,177,810 B2 | 5/2012 | Ferree |
| 8,202,295 B2 | 6/2012 | Kaplan |

(56) References Cited

U.S. PATENT DOCUMENTS

| | | |
|---|---|---|
| 8,202,318 B2 | 6/2012 | Willobee |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,298,284 B2 | 10/2012 | Cassani |
| 8,303,604 B2 | 11/2012 | Stone et al. |
| 8,317,825 B2 | 11/2012 | Stone |
| 8,337,525 B2 | 12/2012 | Stone et al. |
| 8,343,155 B2 | 1/2013 | Fisher et al. |
| 8,343,227 B2 | 1/2013 | Metzger et al. |
| 8,361,113 B2 | 1/2013 | Stone et al. |
| 8,409,253 B2 | 4/2013 | Stone et al. |
| 8,486,114 B2 | 7/2013 | Gillard et al. |
| 8,500,818 B2 | 8/2013 | Metzger et al. |
| 8,506,597 B2 | 8/2013 | Kaiser et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,579,944 B2 | 11/2013 | Holloway et al. |
| 8,597,327 B2 | 12/2013 | Stone et al. |
| 8,608,777 B2 | 12/2013 | Kaiser et al. |
| 8,632,566 B2 | 1/2014 | Olson |
| 8,632,569 B2 | 1/2014 | Stone et al. |
| 8,652,171 B2 | 2/2014 | Stone et al. |
| 8,652,172 B2 | 2/2014 | Denham et al. |
| 8,672,968 B2 | 3/2014 | Stone et al. |
| 8,672,969 B2 | 3/2014 | Stone et al. |
| 8,702,718 B2 | 4/2014 | Bhatnagar et al. |
| 8,721,650 B2 | 5/2014 | Fanton et al. |
| 8,721,684 B2 | 5/2014 | Denham et al. |
| 8,771,316 B2 | 7/2014 | Denham et al. |
| 8,771,352 B2 | 7/2014 | Conner et al. |
| 8,777,956 B2 | 7/2014 | Hoeppner et al. |
| 8,801,783 B2 | 8/2014 | Stone et al. |
| 8,808,374 B2 | 8/2014 | Eggli |
| 8,840,645 B2 | 9/2014 | Denham et al. |
| 8,900,314 B2 | 12/2014 | Metzger et al. |
| 8,926,613 B2 | 1/2015 | Kaiser et al. |
| 8,932,331 B2 | 1/2015 | Kaiser et al. |
| 8,936,621 B2 | 1/2015 | Denham et al. |
| 8,961,548 B2 | 2/2015 | Buser |
| 8,968,364 B2 | 3/2015 | Berelsman et al. |
| 8,998,949 B2 | 4/2015 | Stone et al. |
| 9,005,287 B2 | 4/2015 | Stone |
| 9,017,381 B2 | 4/2015 | Kaiser et al. |
| 9,023,058 B2 | 5/2015 | Jaramillo et al. |
| 9,271,826 B2 | 3/2016 | Eggli et al. |
| 9,289,285 B2 | 3/2016 | Eggli |
| 9,314,235 B2 | 4/2016 | Bojarski et al. |
| 9,314,241 B2 | 4/2016 | Stone et al. |
| 9,357,991 B2 | 6/2016 | Denham et al. |
| 9,357,992 B2 | 6/2016 | Stone et al. |
| 9,370,350 B2 | 6/2016 | Norton |
| 9,381,013 B2 | 7/2016 | Norton |
| 9,402,621 B2 | 8/2016 | Stone et al. |
| 9,408,599 B2 | 8/2016 | Kaiser et al. |
| 9,414,833 B2 | 8/2016 | Stone et al. |
| 9,414,925 B2 | 8/2016 | Metzger et al. |
| 9,468,433 B2 | 10/2016 | Denham et al. |
| 9,486,211 B2 | 11/2016 | Stone et al. |
| 9,492,158 B2 | 11/2016 | Stone et al. |
| 9,498,204 B2 | 11/2016 | Denham et al. |
| 9,504,460 B2 | 11/2016 | Stone et al. |
| 9,510,819 B2 | 12/2016 | Stone et al. |
| 9,510,821 B2 | 12/2016 | Denham et al. |
| 9,532,777 B2 | 1/2017 | Kaiser et al. |
| 9,538,998 B2 | 1/2017 | Stone et al. |
| 9,539,003 B2 | 1/2017 | Stone et al. |
| 9,561,025 B2 | 2/2017 | Stone et al. |
| 9,572,655 B2 | 2/2017 | Denham |
| 9,603,591 B2 | 3/2017 | Denham et al. |
| 2001/0002439 A1 | 5/2001 | Bonutti et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044627 A1 | 11/2001 | Justin |
| 2001/0044639 A1 | 11/2001 | Levinson |
| 2001/0047206 A1 | 11/2001 | Sklar et al. |
| 2001/0051815 A1 | 12/2001 | Esplin |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029048 A1 | 3/2002 | Miller |
| 2002/0029066 A1 | 3/2002 | Foerster |
| 2002/0032465 A1 | 3/2002 | Lemer |
| 2002/0045902 A1 | 4/2002 | Bonutti |
| 2002/0052628 A1 | 5/2002 | Bowman |
| 2002/0055780 A1 | 5/2002 | Sklar |
| 2002/0058966 A1 | 5/2002 | Tormala et al. |
| 2002/0068254 A1 | 6/2002 | Campbell |
| 2002/0077659 A1 | 6/2002 | Johnson et al. |
| 2002/0091391 A1 | 7/2002 | Cole et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0156475 A1 | 10/2002 | Lerch et al. |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0114929 A1 | 6/2003 | Knudsen |
| 2003/0120309 A1 | 6/2003 | Colleran et al. |
| 2003/0130670 A1 | 7/2003 | Anderson et al. |
| 2003/0130694 A1* | 7/2003 | Bojarski ............ A61B 17/0401 606/228 |

(56) References Cited

U.S. PATENT DOCUMENTS

| | | |
|---|---|---|
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0139752 A1 | 7/2003 | Pasricha et al. |
| 2003/0139775 A1 | 7/2003 | Grafton |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208209 A1 | 11/2003 | Gambale et al. |
| 2003/0208210 A1 | 11/2003 | Dreyfuss et al. |
| 2003/0212456 A1 | 11/2003 | Lipchitz et al. |
| 2003/0216809 A1 | 11/2003 | Ferguson |
| 2003/0220646 A1 | 11/2003 | Thelen et al. |
| 2003/0220660 A1 | 11/2003 | Kortenbach et al. |
| 2003/0225459 A1 | 12/2003 | Hammer et al. |
| 2003/0229361 A1 | 12/2003 | Jackson |
| 2003/0229396 A1 | 12/2003 | Andrews |
| 2003/0236555 A1 | 12/2003 | Thornes |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0039389 A1 | 2/2004 | West et al. |
| 2004/0044351 A1 | 3/2004 | Searle |
| 2004/0044391 A1 | 3/2004 | Porter |
| 2004/0059357 A1 | 3/2004 | Koseki |
| 2004/0073176 A1 | 4/2004 | Utterberg |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0127907 A1 | 7/2004 | Dakin et al. |
| 2004/0133206 A1 | 7/2004 | Stevens et al. |
| 2004/0133211 A1 | 7/2004 | Raskin et al. |
| 2004/0133238 A1 | 7/2004 | Cerier |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | McDevitt et al. |
| 2004/0182968 A1 | 9/2004 | Gentry |
| 2004/0187314 A1 | 9/2004 | Johnson |
| 2004/0193185 A1 | 9/2004 | McBrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267317 A1 | 12/2004 | Higgins et al. |
| 2004/0267361 A1 | 12/2004 | Donnelly et al. |
| 2004/0267362 A1 | 12/2004 | Hwang et al. |
| 2005/0004670 A1 | 1/2005 | Gebhardt et al. |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0049598 A1 | 3/2005 | West, Jr. et al. |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0076478 A1 | 4/2005 | Miyazaki et al. |
| 2005/0085819 A1 | 4/2005 | Ellis et al. |
| 2005/0090827 A1 | 4/2005 | Gedebou |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149118 A1 | 7/2005 | Koyfman et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0192632 A1 | 9/2005 | Geissler et al. |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251153 A1 | 11/2005 | Sakamoto et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267479 A1 | 12/2005 | Morgan et al. |
| 2005/0267533 A1 | 12/2005 | Gertner |

(56) References Cited

U.S. PATENT DOCUMENTS

| | | |
|---|---|---|
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004364 A1 | 1/2006 | Green et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0195106 A1 | 8/2006 | Jones et al. |
| 2006/0200235 A1 | 9/2006 | Bianchi et al. |
| 2006/0212055 A1 | 9/2006 | Karabey et al. |
| 2006/0229623 A1 | 10/2006 | Bonutti et al. |
| 2006/0229671 A1 | 10/2006 | Steiner et al. |
| 2006/0229676 A1 | 10/2006 | Doll et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0259076 A1 | 11/2006 | Burkhart et al. |
| 2006/0264944 A1 | 11/2006 | Cole |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276818 A1 | 12/2006 | Buser et al. |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1* | 12/2006 | Bojarski ............ A61B 17/0401 606/232 |
| 2007/0005068 A1 | 1/2007 | Sklar |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0027476 A1 | 2/2007 | Harris et al. |
| 2007/0032800 A1 | 2/2007 | Ortiz et al. |
| 2007/0032823 A1 | 2/2007 | Tegg |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0071568 A1 | 3/2007 | Dorstewitz |
| 2007/0073307 A1 | 3/2007 | Scribner et al. |
| 2007/0073319 A1 | 3/2007 | Mikkaichi et al. |
| 2007/0073322 A1 | 3/2007 | Mikkaichi et al. |
| 2007/0078435 A1 | 4/2007 | Stone et al. |
| 2007/0083236 A1 | 4/2007 | Sikora et al. |
| 2007/0088362 A1 | 4/2007 | Bonutti et al. |
| 2007/0093847 A1 | 4/2007 | Scribner et al. |
| 2007/0100350 A1 | 5/2007 | Deffenbaugh et al. |
| 2007/0112384 A1 | 5/2007 | Conlon et al. |
| 2007/0118217 A1 | 5/2007 | Brulez et al. |
| 2007/0123883 A1 | 5/2007 | Ellis et al. |
| 2007/0123984 A1 | 5/2007 | Hodorek |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0167950 A1 | 7/2007 | Tauro et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198036 A1 | 8/2007 | Sklar et al. |
| 2007/0219558 A1 | 9/2007 | Deutsch |
| 2007/0225715 A1 | 9/2007 | Deffenbaugh et al. |
| 2007/0225719 A1 | 9/2007 | Stone et al. |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0250059 A1 | 10/2007 | Weisshaupt et al. |
| 2007/0250163 A1 | 10/2007 | Cassani |
| 2007/0255282 A1 | 11/2007 | Simonton et al. |
| 2007/0260251 A1 | 11/2007 | Weier et al. |
| 2007/0260279 A1 | 11/2007 | Hotter et al. |
| 2007/0265704 A1 | 11/2007 | Mayer et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2007/0288023 A1 | 12/2007 | Pellegrino et al. |
| 2008/0009904 A1 | 1/2008 | Bourque et al. |
| 2008/0027430 A1 | 1/2008 | Montgomery et al. |
| 2008/0027440 A1 | 1/2008 | Marissen et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0086138 A1 | 4/2008 | Stone et al. |
| 2008/0097430 A1 | 4/2008 | Bernstein et al. |
| 2008/0114460 A1 | 5/2008 | Willobee et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0137624 A1 | 6/2008 | Silverstrim et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0154260 A1 | 6/2008 | Hoof |
| 2008/0154314 A1 | 6/2008 | McDevitt |

(56) References Cited

U.S. PATENT DOCUMENTS

| | | |
|---|---|---|
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0172097 A1 | 7/2008 | Lerch et al. |
| 2008/0177302 A1 | 7/2008 | Shurnas |
| 2008/0183290 A1 | 7/2008 | Baird et al. |
| 2008/0188933 A1 | 8/2008 | Koob et al. |
| 2008/0188935 A1 | 8/2008 | Saylor et al. |
| 2008/0188936 A1 | 8/2008 | Ball et al. |
| 2008/0208252 A1 | 8/2008 | Holmes |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0228271 A1 | 9/2008 | Stone et al. |
| 2008/0234730 A1 | 9/2008 | Cotton et al. |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275469 A1 | 11/2008 | Fanton et al. |
| 2008/0275477 A1 | 11/2008 | Sterrett et al. |
| 2008/0281428 A1 | 11/2008 | Meyers et al. |
| 2008/0288070 A1 | 11/2008 | Lo |
| 2008/0300611 A1 | 12/2008 | Houser et al. |
| 2008/0312689 A1 | 12/2008 | Denham et al. |
| 2008/0319478 A1 | 12/2008 | Foerster et al. |
| 2009/0018589 A1 | 1/2009 | Smisson, III et al. |
| 2009/0018654 A1 | 1/2009 | Schmieding et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062847 A1 | 3/2009 | Ken |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0182335 A1 | 7/2009 | Struhl |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228015 A1 | 9/2009 | Ellis |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0234451 A1 | 9/2009 | Manderson |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0265015 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0312793 A1 | 12/2009 | Huxel et al. |
| 2009/0318960 A1 | 12/2009 | Burkhart |
| 2009/0318961 A1 | 12/2009 | Stone et al. |
| 2010/0016899 A1 | 1/2010 | Gelfand |
| 2010/0042114 A1 | 2/2010 | Schaffhausen |
| 2010/0063541 A1 | 3/2010 | Brunelle et al. |
| 2010/0087857 A1 | 4/2010 | Stone et al. |
| 2010/0094355 A1 | 4/2010 | Trenhaile |
| 2010/0106254 A1 | 4/2010 | Delsignore |
| 2010/0121348 A1 | 5/2010 | Van Der Burg et al. |
| 2010/0145384 A1 | 6/2010 | Stone et al. |
| 2010/0152752 A1 | 6/2010 | Denove et al. |
| 2010/0191342 A1 | 7/2010 | Byrd et al. |
| 2010/0211071 A1 | 8/2010 | Lettmann et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2010/0324676 A1 | 12/2010 | Albertorio |
| 2010/0331881 A1 | 12/2010 | Hart |
| 2011/0009885 A1 | 1/2011 | Graf et al. |
| 2011/0022083 A1 | 1/2011 | Dimatteo et al. |
| 2011/0026141 A1 | 2/2011 | Barrows |
| 2011/0046733 A1 | 2/2011 | Eggli |
| 2011/0087225 A1 | 4/2011 | Fritzinger |
| 2011/0087280 A1 | 4/2011 | Albertorio |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0112537 A1 | 5/2011 | Bernstein et al. |
| 2011/0112538 A1 | 5/2011 | Dell'Oca |
| 2011/0160767 A1 | 6/2011 | Stone et al. |
| 2011/0160768 A1 | 6/2011 | Stone et al. |
| 2011/0184227 A1 | 7/2011 | Altman et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2011/0295284 A1 | 12/2011 | Purdue et al. |
| 2012/0004669 A1 | 1/2012 | Overes et al. |
| 2012/0041485 A1 | 2/2012 | Kaiser et al. |
| 2012/0041486 A1 | 2/2012 | Stone et al. |
| 2012/0041496 A1 | 2/2012 | Walker |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0059468 A1 | 3/2012 | Mattern et al. |
| 2012/0089193 A1 | 4/2012 | Stone et al. |
| 2012/0095470 A1 | 4/2012 | Kaiser et al. |
| 2012/0109156 A1 | 5/2012 | Overes et al. |
| 2012/0116409 A1 | 5/2012 | Stone |
| 2012/0116450 A1 | 5/2012 | McDevitt et al. |
| 2012/0116452 A1 | 5/2012 | Stone et al. |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0130492 A1 | 5/2012 | Eggli et al. |
| 2012/0143215 A1 | 6/2012 | Corrao et al. |
| 2012/0150223 A1 | 6/2012 | Manos et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0215257 A1 | 8/2012 | McDevitt et al. |
| 2012/0245585 A1 | 9/2012 | Kaiser et al. |
| 2012/0265219 A1 | 10/2012 | Rushdy et al. |
| 2012/0290003 A1 | 11/2012 | Dreyfuss |
| 2012/0290004 A1 | 11/2012 | Lombardo et al. |
| 2012/0296427 A1 | 11/2012 | Conner et al. |
| 2012/0310245 A1 | 12/2012 | Hoeppner et al. |
| 2013/0018375 A1 | 1/2013 | Dell'Oca |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |

(56) References Cited

U.S. PATENT DOCUMENTS

| | | |
|---|---|---|
| 2013/0035722 A1 | 2/2013 | McDevitt et al. |
| 2013/0046341 A1 | 2/2013 | Stone et al. |
| 2013/0090731 A1 | 4/2013 | Walker |
| 2013/0103082 A1 | 4/2013 | Kaiser et al. |
| 2013/0110165 A1 | 5/2013 | Burkhart et al. |
| 2013/0110251 A1 | 5/2013 | Metzger et al. |
| 2013/0116730 A1 | 5/2013 | Denham et al. |
| 2013/0123810 A1 | 5/2013 | Brown et al. |
| 2013/0123813 A1 | 5/2013 | Stone et al. |
| 2013/0131722 A1 | 5/2013 | Marchand et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158601 A1 | 6/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0237997 A1 | 9/2013 | Arai et al. |
| 2013/0245761 A1 | 9/2013 | Conner et al. |
| 2013/0274812 A1 | 10/2013 | Dell'Oca |
| 2013/0289564 A1 | 10/2013 | Bernstein et al. |
| 2013/0317621 A1 | 11/2013 | Metzger et al. |
| 2013/0331848 A1 | 12/2013 | Kaiser et al. |
| 2014/0046367 A1 | 2/2014 | Stone et al. |
| 2014/0046368 A1 | 2/2014 | Kaiser et al. |
| 2014/0067081 A1 | 3/2014 | Stone |
| 2014/0088655 A1 | 3/2014 | Stone et al. |
| 2014/0094913 A1 | 4/2014 | Berelsman et al. |
| 2014/0135835 A1 | 5/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0257378 A1 | 9/2014 | Norton et al. |
| 2014/0276992 A1 | 9/2014 | Stone et al. |
| 2014/0277447 A1 | 9/2014 | Berelsman et al. |
| 2014/0324101 A1 | 10/2014 | Denham et al. |
| 2014/0330311 A1 | 11/2014 | Denham et al. |
| 2014/0336760 A1 | 11/2014 | Eggli |
| 2014/0350674 A1 | 11/2014 | Stone et al. |
| 2015/0012094 A1 | 1/2015 | Denham et al. |
| 2015/0057757 A1 | 2/2015 | Metzger et al. |
| 2015/0119890 A1 | 4/2015 | Kaiser et al. |
| 2015/0127051 A1 | 5/2015 | Kaiser et al. |
| 2015/0134000 A1 | 5/2015 | Denham et al. |
| 2015/0173887 A1 | 6/2015 | Berelsman et al. |
| 2015/0257750 A1 | 9/2015 | Kaiser et al. |
| 2016/0000483 A1 | 1/2016 | Stone |
| 2016/0022261 A1 | 1/2016 | Stone et al. |
| 2016/0058436 A1 | 3/2016 | Stone et al. |
| 2016/0081789 A1 | 3/2016 | Denham et al. |
| 2016/0106414 A1 | 4/2016 | Stone et al. |
| 2016/0128684 A1 | 5/2016 | Stone et al. |
| 2016/0183935 A1 | 6/2016 | Stone |
| 2016/0199053 A1 | 7/2016 | Norton et al. |
| 2016/0213369 A1 | 7/2016 | Stone et al. |
| 2016/0242760 A1 | 8/2016 | Kaiser et al. |
| 2017/0014225 A1 | 1/2017 | Denham et al. |
| 2017/0020507 A1 | 1/2017 | Denham et al. |
| 2017/0035411 A1 | 2/2017 | Kaiser et al. |
| 2017/0049557 A1 | 2/2017 | Denham et al. |
| 2017/0065278 A1 | 3/2017 | Stone |
| 2017/0071593 A1 | 3/2017 | Stone |
| 2017/0071595 A1 | 3/2017 | Stone et al. |

FOREIGN PATENT DOCUMENTS

| | | |
|---|---|---|
| AU | 5850469 | 1/1971 |
| AU | 5850469 A | 1/1971 |
| AU | 5963869 | 2/1971 |
| AU | 5963869 A | 2/1971 |
| AU | 1505470 | 11/1971 |
| AU | 1505470 A | 11/1971 |
| AU | 2223767 | 5/1973 |
| AU | 3615171 | 5/1973 |
| AU | 5028569 | 9/1973 |
| AU | 7110887 | 10/1987 |
| AU | 7110887 A | 10/1987 |
| AU | 639410 | 11/1989 |
| AU | 651929 | 8/1994 |
| BE | 1010569 A6 | 10/1998 |
| CN | 1720872 A | 1/2006 |
| CN | 1777450 A | 5/2006 |
| CN | 101083954 A | 12/2007 |
| CN | 101584592 A | 11/2009 |
| CN | 105208970 A | 12/2015 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 C | 2/1986 |
| DE | 4127550 | 2/1993 |
| DE | 4302397 | 7/1993 |
| DE | 29621340 | 5/1998 |
| DE | 19841252 | 3/2000 |
| DE | 20207781 U1 | 8/2002 |
| EP | 19062 A1 | 11/1980 |
| EP | 0108912 | 5/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0490417 | 6/1992 |
| EP | 0497079 | 8/1992 |
| EP | 0502509 | 9/1992 |
| EP | 0502698 | 9/1992 |
| EP | 520177 | 12/1992 |
| EP | 520177 A1 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| EP | 2238944 A2 | 10/2010 |
| EP | 2544607 A1 | 1/2013 |
| EP | 2709557 A1 | 3/2014 |
| EP | 2934379 A1 | 10/2015 |
| EP | 2434987 B1 | 6/2016 |
| FR | 2622790 | 5/1989 |
| FR | 2655840 | 6/1991 |

(56) References Cited

FOREIGN PATENT DOCUMENTS

| | | |
|---|---|---|
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| GB | 2454251 A | 5/2009 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62159647 U | 10/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9609797 A1 | 4/1996 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9937219 A1 | 7/1999 |
| WO | WO-9944544 | 9/1999 |
| WO | WO-9952472 A1 | 10/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-03092551 A1 | 11/2003 |
| WO | WO-2004091412 A1 | 10/2004 |
| WO | WO-2005104992 A1 | 11/2005 |
| WO | WO-2005122954 | 12/2005 |
| WO | WO-2006011786 A1 | 2/2006 |
| WO | WO-2006023661 A2 | 3/2006 |
| WO | WO-2006023661 A2 | 3/2006 |
| WO | WO-2006055823 A2 | 5/2006 |
| WO | WO-2007045460 A2 | 4/2007 |
| WO | WO-2007103562 A2 | 9/2007 |
| WO | WO-2007109280 A2 | 9/2007 |
| WO | WO-2007119057 A1 | 10/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2009083047 A1 | 7/2009 |
| WO | WO-2009131820 A1 | 10/2009 |
| WO | WO-2010138832 A1 | 12/2010 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |
| WO | WO-2013066974 A1 | 5/2013 |
| WO | WO-2013074525 A1 | 5/2013 |
| WO | WO-2014/100109 A1 | 6/2014 |
| WO | WO-2014151766 A1 | 9/2014 |

OTHER PUBLICATIONS

Ziptight™ Fixation System Featuring Zip Loop™ Technology. Ankle Syndesmosis. Surgical Protocol by Timothy Charlton, M.D. Biomet Sports® Medicine brochure. (Jun. 15, 2011) 8 pages.

"U.S. Appl. No. 11/504,882, Supplemental Notice of Allowability dated Mar. 12, 2015", 5 pgs.

"U.S. Appl. No. 11/541,505, Notice of Allowance dated Sep. 18, 2009", 8 pgs.

"U.S. Appl. No. 11/541,506, Notice of Allowance dated Jun. 1, 2009", 10 pgs.

"U.S. Appl. No. 12/196,405, Notice of Allowance dated Oct. 26, 2011", 11 pgs.

"U.S. Appl. No. 12/196,407, Examiner Interview Summary dated Jul. 14, 2011", 3 pgs.

"U.S. Appl. No. 12/196,407, Notice of Allowance dated Oct. 26, 2011", 10 pgs.

"U.S. Appl. No. 12/196,410, Examiner Interview Summary dated Jul. 14, 2011", 3 pgs.

"U.S. Appl. No. 12/196,410, Notice of Allowance dated Oct. 13, 2011", 8 pgs.

"U.S. Appl. No. 12/719,337, Notice of Allowance dated Mar. 11, 2015", 10 pgs.

"U.S. Appl. No. 13/098,897, Examiner Interview Summary dated Nov. 27, 2012", 3 pgs.

"U.S. Appl. No. 13/098,897, Non Final Office Action dated Sep. 21, 2012", 9 pgs.

"U.S. Appl. No. 13/098,927, Advisory Action dated Aug. 8, 2013", 3 pgs.

"U.S. Appl. No. 13/098,927, Applicant's Summary of Examiner Interview filed Sep. 23, 2013", 12 pgs.

"U.S. Appl. No. 13/098,927, Examiner Interview Summary dated Jun. 28, 2013", 3 pgs.

"U.S. Appl. No. 13/098,927, Examiner Interview Summary dated Sep. 20, 2013", 3 pgs.

"U.S. Appl. No. 13/098,927, Final Office Action dated May 22, 2013", 10 pgs.

"U.S. Appl. No. 13/098,927, Non Final Office Action dated Sep. 24, 2012", 12 pgs.

"U.S. Appl. No. 13/098,927, Notice of Allowance dated Jan. 8, 2014", 5 pgs.

"U.S. Appl. No. 13/098,927, Notice of Allowance dated Sep. 26. 2013", 14 pgs.

"U.S. Appl. No. 13/098,927, Response filed Jul. 22, 2015 to Final Office Action dated May 22, 2013", 17 pgs.

"U.S. Appl. No. 13/098,927, Response filed Aug. 27, 2012 to Restriction Requirement dated Jul. 25, 2012", 14 pgs.

"U.S. Appl. No. 13/098,927, Response filed Dec. 21, 2012 to Non Final Office Action dated Sep. 24, 2012", 21 pgs.

"U.S. Appl. No. 13/098,927, Restriction Requirement dated Jul. 25, 2012", 8 pgs.

"U.S. Appl. No. 13/102,182, Notice of Allowance dated Mar. 22, 2012", 10 pgs.

"U.S. Appl. No. 13/109,672,312 Amendment filed Jan. 15, 2015", 3 pgs.

"U.S. Appl. No. 13/109,672, Notice of Allowance dated Feb. 3, 2015", 2 pgs.

(56) References Cited

OTHER PUBLICATIONS

"U.S. Appl. No. 13/109,672, PTO Response to Rule 312 Communication dated Jan. 27, 2015", 2 pgs.
"U.S. Appl. No. 13/181,729, Non Final Office Action dated Oct. 2, 2012", 7 pgs.
"U.S. Appl. No. 13/281,009, Non Final Office Action dated Jun. 2, 2015", 9 pgs.
"U.S. Appl. No. 13/281,009, Notice of Allowance dated Feb. 24, 2016", 9 pgs.
"U.S. Appl. No. 13/281,009, Notice of Allowance dated Oct. 29, 2015", 8 pgs.
"U.S. Appl. No. 13/281,009, Response filed Sep. 2, 2015 to Non Final Office Action dated Jun. 2, 2015", 13 pgs.
"U.S. Appl. No. 13/288,459, Examiner Interview Summary dated Feb. 6, 2015", 3 pgs.
"U.S. Appl. No. 13/288,459, Non Final Office Action dated Jun. 24, 2015", 10 pgs.
"U.S. Appl. No. 13/288,459, Notice of Allowance dated Jan. 11, 2016", 13 pgs.
"U.S. Appl. No. 13/288,459, Response filed Mar. 3, 2015 to Non Final Office Action dated Nov. 4, 2014", 16 pgs.
"U.S. Appl. No. 13/288,459, Response filed Oct. 23, 2015 to Non Final Office Action dated Jun. 24, 2015", 14 pgs.
"U.S. Appl. No. 13/293,825, Notice of Allowability dated Jun. 22, 2015", 7 pgs.
"U.S. Appl. No. 13/293,825, Notice of Allowance dated May 19, 2015", 9 pgs.
"U.S. Appl. No. 13/293,825, Response filed Apr. 15, 2015 to Restriction Requirement dated Feb. 12, 2015", 17 pgs.
"U.S. Appl. No. 13/295,126, Non Final Office Action dated May 19, 2015", 9 pgs.
"U.S. Appl. No. 13/295,126, Notice of Allowance dated Oct. 22, 2015", 9 pgs.
"U.S. Appl. No. 13/295,126, Response filed Apr. 13, 2015 to Restriction Requirement dated Feb. 12, 2015", 1 pgs.
"U.S. Appl. No. 13/295,126, Response filed Aug. 17, 2015 to Non Final Office Action dated May 19, 2015", 21 pgs.
"U.S. Appl. No. 13/311,936, Examiner Interview Summary dated Feb. 12, 2015", 2 pgs.
"U.S. Appl. No. 13/311,936, Non Final Office Action dated Oct. 19, 2015", 8 pgs.
"U.S. Appl. No. 13/311,936, Notice of Allowance dated Mar. 29, 2016", 8 pgs.
"U.S. Appl. No. 13/311,936, Response filed Jan. 18, 2016 to Non Final Office Action dated Oct. 19, 2015", 8 pgs.
"U.S. Appl. No. 13/311,936, Response filed Jun. 9, 2015 to Non Final Office Action dated Feb. 9, 2015", 12 pgs.
"U.S. Appl. No. 13/350,985, Final Office Action dated Apr. 16, 2015", 8 pgs.
"U.S. Appl. No. 13/350,985, Notice of Allowance dated Jul. 27, 2015", 5 pgs.
"U.S. Appl. No. 13/350,985, Response filed Mar. 13, 2015 to Non Final Office Action dated Dec. 15, 2014", 10 pgs.
"U.S. Appl. No. 13/350,985, Response filed Jul. 9, 2015 to Final Office Action dated Apr. 16, 2015", 8 pgs.
"U.S. Appl. No. 13/399,125, Non Final Office Action dated Oct. 24, 2012", 12 pgs.
"U.S. Appl. No. 13/412,116, Non Final Office Action dated Sep. 11, 2013", 9 pgs.
"U.S. Appl. No. 13/412,127, Non Final Office Action dated Aug. 7, 2013", 15 pgs.
"U.S. Appl. No. 13/587,374, Non Final Office Action dated Jul. 17, 2013", 8 pgs.
"U.S. Appl. No. 13/625,413, Final Office Action dated Oct. 30, 2015", 8 pgs.
"U.S. Appl. No. 13/625,413, Non Final Office Action dated Jun. 8, 2015", 11 pgs.
"U.S. Appl. No. 13/625,413, Notice of Allowance dated Apr. 1, 2016", 8 pgs.
"U.S. Appl. No. 13/625,413, Notice of Allowance dated Dec. 11, 2015", 9 pgs.
"U.S. Appl. No. 13/625,413, Response filed May 11, 2015 to Restriction Requirement dated Mar. 10, 2015", 1 pg.
"U.S. Appl. No. 13/625,413, Response filed Sep. 8, 2015 to Non Final Office Action dated Jun. 8, 2015", 16 pgs.
"U.S. Appl. No. 13/625,413, Response filed Dec. 1, 2015 to Final Office Action dated Oct. 30, 2015", 9 pgs.
"U.S. Appl. No. 13/645,964, Advisory Action dated Feb. 4, 2016", 2 pgs.
"U.S. Appl. No. 13/645,964, Final Office Action dated Oct. 6, 2015", 17 pgs.
"U.S. Appl. No. 13/645,964, Non Final Office Action dated Mar. 15, 2016", 15 pgs.
"U.S. Appl. No. 13/645,964, Non Final Office Action dated Mar. 17, 2015", 15 pgs.
"U.S. Appl. No. 13/645,964, Response filed Jul. 17, 2015 to Non Final Office Action dated Mar. 17, 2015", 17 pgs.
"U.S. Appl. No. 13/645,964, Response filed Dec. 4, 2015 to Final Office Action dated Oct. 6, 2015", 14 pgs.
"U.S. Appl. No. 13/656,821, Notice of Allowance dated Jun. 18, 2015", 11 pgs.
"U.S. Appl. No. 13/656,821, Response filed May 11, 2015 to Restriction Requirement dated Mar. 10, 2015", 1 pg.
"U.S. Appl. No. 13/656,821, Restriction Requirement dated Mar. 10, 2015", 6 pgs.
"U.S. Appl. No. 13/720,648, Final Office Action dated Nov. 16, 2015", 7 pgs.
"U.S. Appl. No. 13/720,648, Non Final Office Action dated Jun. 10, 2015", 11 pgs.
"U.S. Appl. No. 13/720,648, Notice of Allowance dated Feb. 5, 2016", 11 pgs.
"U.S. Appl. No. 13/720,648, Response filed Jan. 13, 2016 to Final Office Action dated Nov. 16, 2015", 9 pgs.
"U.S. Appl. No. 13/720,648, Response filed May 11, 2015 to Restriction Requirement dated Mar. 10, 2015", 8 pgs.
"U.S. Appl. No. 13/720,648, Response filed Oct. 9, 2015 to Non Final Office Action dated Jun. 10, 2015", 12 pgs.
"U.S. Appl. No. 13/720,648, Restriction Requirement dated Mar. 10, 2015", 8 pgs.
"U.S. Appl. No. 13/751,846, Final Office Action dated Nov. 17, 2015", 9 pgs.
"U.S. Appl. No. 13/751,846, Non Final Office Action dated Jun. 15, 2015", 10 pgs.
"U.S. Appl. No. 13/751,846, Notice of Allowance dated Mar. 16, 2016", 11 pgs.
"U.S. Appl. No. 13/751,846, Response filed Feb. 5, 2016 to Final Office Action dated Nov. 17, 2015", 14 pgs.
"U.S. Appl. No. 13/751,846, Response filed May 11, 2015 to Restriction Requirement dated Mar. 10, 2015", 15 pgs.
"U.S. Appl. No. 13/751,846, Response filed Oct. 9, 2015 to Non Final Office Action dated Jun. 15, 2015", 20 pgs.
"U.S. Appl. No. 13/757,003, Non Final Office Action dated Jun. 25, 2015", 8 pgs.
"U.S. Appl. No. 13/757,003, Notice of Allowance dated Feb. 8, 2016", 10 pgs.
"U.S. Appl. No. 13/757,003, Response filed May 12, 2015 to Restriction Requirement dated Mar. 12, 2015", 9 pgs.
"U.S. Appl. No. 13/757,003, Response filed Oct. 26, 2015 to Non Final Office Action dated Jul. 25, 2015", 8 pgs.
"U.S. Appl. No. 13/757,019, Non Final Office Action dated Jun. 25, 2015", 11 pgs.
"U.S. Appl. No. 13/757,019, Notice of Allowance dated Dec. 10, 2015", 10 pgs.
"U.S. Appl. No. 13/757,019, Response filed May 11, 2015 to Restriction Requirement dated Mar. 11, 2015", 9 pgs.
"U.S. Appl. No. 13/757,019, Response filed Oct. 26, 2015 to Non Final Office Action dated Jun. 25, 2015", 9 pgs.
"U.S. Appl. No. 13/767,401, Non Final Office Action dated Aug. 26, 2015", 9 pgs.
"U.S. Appl. No. 13/767,401, Notice of Allowance dated Apr. 8, 2016", 9 pgs.

(56) References Cited

OTHER PUBLICATIONS

"U.S. Appl. No. 13/767,401, Notice of Allowance dated Dec. 30, 2015", 9 pgs.
"U.S. Appl. No. 13/767,401, Response filed May 18, 2015 to Restriction Requirement dated Mar. 17, 2015", 15 pgs.
"U.S. Appl. No. 13/767,401, Response filed Nov. 6, 2015 to Non Final Office Action dated Aug. 26, 2015", 12 pgs.
"U.S. Appl. No. 13/767,401, Restriction Requirement dated Mar. 17, 2015", 8 pgs.
"U.S. Appl. No. 13/790,982, Examiner Interview Summary dated Jun. 9, 2015", 3 pgs.
"U.S. Appl. No. 13/790,982, Non Final Office Action dated Sep. 16, 2015", 11 pgs.
"U.S. Appl. No. 13/790,982, Notice of Allowance dated Feb. 24, 2016", 10 pgs.
"U.S. Appl. No. 13/790,982, Response filed Jun. 2, 2015 to Restriction Requirement dated Apr. 2, 2015", 11 pgs.
"U.S. Appl. No. 13/790,982, Response filed Dec. 16, 2015 to Non Final Office Action dated Sep. 16, 2015", 10 pgs.
"U.S. Appl. No. 13/790,982, Restriction Requirement dated Apr. 2, 2015", 10 pgs.
"U.S. Appl. No. 13/790,997, Examiner Interview Summary dated Jun. 8, 2015", 3 pgs.
"U.S. Appl. No. 13/790,997, Non Final Office Action dated Sep. 21, 2015", 8 pgs.
"U.S. Appl. No. 13/790,997, Notice of Allowance dated Mar. 2, 2016", 9 pgs.
"U.S. Appl. No. 13/790,997, Response filed Jun. 2, 2015 to Restriction Requirement dated Apr. 2, 2015", 12 pgs.
"U.S. Appl. No. 13/790,997, Response filed Dec. 18, 2015 to Non Final Office Action dated Sep. 21, 2015", 9 pgs.
"U.S. Appl. No. 13/790,997, Restriction Requirement dated Apr. 2, 2015", 8 pgs.
"U.S. Appl. No. 13/833,567, Final Office Action dated Mar. 9, 2016", 9 pgs.
"U.S. Appl. No. 13/833,567, Non Final Office Action dated Oct. 23, 2015", 10 pgs.
"U.S. Appl. No. 13/833,567, Response filed Jan. 22, 2016 to Non Final Office Action dated Oct. 23, 2015", 11 pgs.
"U.S. Appl. No. 13/833,567, Response filed Jun. 25, 2015 to Restriction Requirement dated Apr. 3, 2015", 10 pgs.
"U.S. Appl. No. 13/833,567, Restriction Requirement dated Apr. 3, 2015", 6 pgs.
"U.S. Appl. No. 13/838,755, Final Office Action dated Feb. 22, 2016", 9 pgs.
"U.S. Appl. No. 13/838,755, Non Final Office Action dated Sep. 18, 2015", 11 pgs.
"U.S. Appl. No. 13/838,755, Response filed Jun. 8, 2015 to Restriction Requirement dated Apr. 6, 2015", 1 pg.
"U.S. Appl. No. 13/838,755, Response filed Dec. 1, 2015 to Non Final Office Action dated Sep. 17, 2015", 13 pgs.
"U.S. Appl. No. 13/838,755, Restriction Requirement dated Apr. 6, 2015", 6 pgs.
"U.S. Appl. No. 13/889,851, Non Final Office Action dated Apr. 6, 2015", 10 pgs.
"U.S. Appl. No. 13/889,851, Notice of Allowance dated Aug. 12, 2015", 8 pgs.
"U.S. Appl. No. 13/889,851, Response filed Feb. 26, 2015 to Restriction Requirement dated Jan. 21, 2015", 12 pgs.
"U.S. Appl. No. 13/889,851, Response filed Jul. 6, 2015 to Non Final Office Action dated Apr. 6, 2015", 14 pgs.
"U.S. Appl. No. 13/889,851, Restriction Requirement dated Jan. 21, 2015", 6 pgs.
"U.S. Appl. No. 13/889,851, Supplemental Amendment and Response filed Jul. 6, 2015 to Non Final Office Action dated Apr. 6, 2015", 8 pgs.
"U.S. Appl. No. 13/959,145, Examiner Interview Summary dated Sep. 16, 2015", 3 pgs.
"U.S. Appl. No. 13/959,145, Final Office Action dated Jan. 29, 2016", 16 pgs.
"U.S. Appl. No. 13/959,145, Final Office Action dated Feb. 5, 2015", 22 pgs.
"U.S. Appl. No. 13/959,145, Non Final Office Action dated Jul. 31, 2015", 21 pgs.
"U.S. Appl. No. 13/959,145, Notice of Allowance dated Apr. 13, 2016", 5 pgs.
"U.S. Appl. No. 13/959,145, Response filed Mar. 28, 2016 to Final Office Action dated Jan. 29, 2016", 10 pgs.
"U.S. Appl. No. 13/959,145, Response filed Jul. 6, 2015 to Final Office Action dated Feb. 5, 2015", 18 pgs.
"U.S. Appl. No. 13/959,145, Response filed Oct. 30, 2015 to Non Final Office Action dated Jul. 31, 2015", 14 pgs.
"U.S. Appl. No. 14/055,172, Restriction Requirement dated Mar. 4, 2016", 6 pgs.
"U.S. Appl. No. 14/055,191, Restriction Requirement dated Mar. 7, 2016", 6 pgs.
"U.S. Appl. No. 14/071,295, Supplemental Notice of Allowability dated Jan. 26, 2015", 2 pgs.
"U.S. Appl. No. 14/107,350, Notice of Allowance dated Feb. 26, 2016", 11 pgs.
"U.S. Appl. No. 14/211,977, Preliminary Amendment filed Mar. 2, 2016", 7 pgs.
"U.S. Appl. No. 14/211,977, Restriction Requirement dated Mar. 11, 2016", 6 pgs.
"U.S. Appl. No. 14/275,548, Non Final Office Action dated Feb. 19, 2016", 14 pgs.
"U.S. Appl. No. 14/324,688, Non Final Office Action dated Jan. 8, 2016", 18 pgs.
"U.S. Appl. No. 14/324,688, Response filed Apr. 8, 2016 to Non Final Office Action dated Jan. 8, 2016", 15 pgs.
"U.S. Appl. No. 14/456,286, Non Final Office Action dated Dec. 30, 2015", 16 pgs.
"U.S. Appl. No. 14/456,286, Response filed Mar. 30, 2016 to Non Final Office Action dated Dec. 30, 2015", 15 pgs.
"U.S. Appl. No. 14/456,286, Response filed Dec. 11, 2015 to Restriction Requirement dated Oct. 29, 2015", 6 pgs.
"U.S. Appl. No. 14/456,286, Restriction Requirement dated Oct. 29, 2015", 9 pgs.
"U.S. Appl. No. 14/589,101, Final Office Action dated Oct. 2, 2015", 10 pgs.
"U.S. Appl. No. 14/589,101, Non Final Office Action dated Feb. 12, 2015", 10 pgs.
"U.S. Appl. No. 14/589,101, Response filed Jun. 12, 2015 to Non Final Office Action dated Feb. 12, 2015", 11 pgs.
"U.S. Appl. No. 14/589,101, Response filed Dec. 29, 2015 to Final Office Action dated Oct. 2, 2015", 15 pgs.
"U.S. Appl. No. 14/697,140, Non Final Office Action dated Apr. 8, 2016", 8 pgs.
"U.S. Appl. No. 14/794,309, Preliminary Amendment filed Sep. 22, 2015", 6 pgs.
"U.S. Appl. No. 14/794,309, Supplemental Preliminary Amendment filed Mar. 3, 2016", 8 pgs.
"U.S. Appl. No. 14/876,167, Preliminary Amendment filed Oct. 27, 2015", 8 pgs.
"U.S. Appl. No. 14/936,831, Preliminary Amendment filed Nov. 11, 2015", 6 pgs.
"U.S. Appl. No. 14/956,724, Preliminary Amendment filed Dec. 7, 2015", 8 pgs.
"U.S. Appl. No. 14/956,724, Supplemental Preliminary Amendment filed Feb. 11, 2016", 7 pgs.
"U.S. Appl. No. 14/983,108, Preliminary Amendment filed Dec. 30, 2015", 7 pgs.
"U.S. Appl. No. 14/983,747, Preliminary Amendment filed Jan. 4, 2016", 5 pgs.
"U.S. Appl. No. 15/060,007, Preliminary Amendment filed Mar. 9, 2016", 9 pgs.
"U.S. Appl. No. 15/061,352, Preliminary Amendment filed Mar. 7, 2016", 8 pgs.
"U.S. Appl. No. 15/074,553, Preliminary Amendment filed Mar. 21, 2016", 8 pgs.
"Bio-Intrafix Tibial Soft Tissue Fastener, Building on the Legacy of IntraFix", DePuy Mitek brochure, (Feb. 2007), 6 pgs.

(56) References Cited

OTHER PUBLICATIONS

"European Application Serial No. 10727548.9, Office Action dated Jan. 11, 2016", 6 pgs.
"European Application Serial No. 10727548.9, Response filed Mar. 19, 2015 to Examination Notification Art. 94(3) dated Sep. 18, 2014", 23 pgs.
"European Application Serial No. 11707316.3, Office Action dated Nov. 10, 2015", 6 pgs.
"European Application Serial No. 11707316.3, Response filed Jun. 29, 2015 to Examination Notification Art. 94(3) dated Dec. 17, 2014", 25 pgs.
"European Application Serial No. 12721676.0, Communication pursuant to Article 94(3) EPC dated Sep. 30, 2015", 4 pgs.
"European Application Serial No. 12791902.5, Examination Notification Art. 94(3) dated Aug. 14, 2015", 4 pgs.
"European Application Serial No. 12806211.4, Examination Notification Art 94(3) dated Aug. 13, 2015", 5 pgs.
"European Application Serial No. 13818131.8, Office Action dated Jul. 28, 2015", 2 pgs.
"European Application Serial No. 13818131.8, Response filed Feb. 8, 2016 to Office Action dated Jul. 28, 2015", 14 pgs.
"European Application Serial No. 14716173.1, Office Action dated Nov. 5, 2015", 2 pgs.
"International Application Serial No. PCT/US2013/075989, International Preliminary Report on Patentability dated Jul. 2, 2015", 10 pgs.
"International Application Serial No. PCT/US2014/026413, International Preliminary Report on Patentability dated Sep. 24, 2015", 10 pgs.
"PANALOK Anchor with PDS II and ETHIBOND Suture", Mitek Products ETHICON, (1997), 2 pgs.
"U.S. Appl. No. 13/281,009, Notice of Allowance dated Jun. 23, 2016", 9 pgs.
"U.S. Appl. No. 13/288,459, Notice of Allowance dated May 10, 2016", 7 pgs.
"U.S. Appl. No. 13/311,936, PTO Response to Rule 312 Communication dated May 10, 2016", 2 pgs.
"U.S. Appl. No. 13/645,964, Response filed Jun. 13, 2016 to Non Final Office Action dated Mar. 15, 2016", 11 pgs.
"U.S. Appl. No. 13/833,567, Advisory Action dated Apr. 28, 2016", 3 pgs.
"U.S. Appl. No. 13/833,567, Non Final Office Action dated May 27, 2016", 9 pgs.
"U.S. Appl. No. 13/838,755, Notice of Allowance dated Apr. 27, 2016", 7 pgs.
"U.S. Appl. No. 13/959,145, Notice of Allowability dated Jun. 14, 2016", 2 pgs.
"U.S. Appl. No. 14/055,172, Response filed May 4, 2016 to Restriction Requirement dated Mar. 4, 2016", 8 pgs.
"U.S. Appl. No. 14/055,191, Non Final Office Action dated May 16, 2016", 8 pgs.
"U.S. Appl. No. 14/055,191, Response filed Apr. 29, 2016 to Restriction Requirement dated Mar. 7, 2016", 8 pgs.
"U.S. Appl. No. 14/094,311, Restriction Requirement dated Jun. 22, 2016", 6 pgs.
"U.S. Appl. No. 14/159,094, Response filed Jun. 3, 2016 to Restriction Requirement dated Apr. 20, 2016", 9 pgs.
"U.S. Appl. No. 14/159,094, Restriction Requirement dated Apr. 20, 2016", 6 pgs.
"U.S. Appl. No. 14/182,046, Restriction Requirement dated Apr. 26, 2016", 6 pgs.
"U.S. Appl. No. 14/211,977, Response filed Apr. 29, 2016 to Restriction Requirement dated Mar. 11, 2016", 8 pgs.
"U.S. Appl. No. 14/215,550, Response filed Jun. 22, 2016 to Restriction Requirement dated Apr. 28, 2016", 7 pgs.
"U.S. Appl. No. 14/215,550, Restriction Requirement dated Apr. 28, 2016", 6 pgs.
"U.S. Appl. No. 14/275,548, Examiner Interview Summary dated May 25, 2016", 3 pgs.
"U.S. Appl. No. 14/275,548, Response filed May 19, 2016 to Non Final Office Action dated Feb. 19, 2016", 19 pgs.
"U.S. Appl. No. 14/324,688, Notice of Allowance dated Jun. 9, 2016", 7 pgs.
"U.S. Appl. No. 14/456,286, Advisory Action dated Jun. 21, 2016", 3 pgs.
"U.S. Appl. No. 14/456,286, Final Office Action dated May 27, 2016", 15 pgs.
"U.S. Appl. No. 14/456,286, Response filed Jun. 13, 2016 to Final Office Action dated May 27, 2016", 10 pgs.
"U.S. Appl. No. 14/589,101, Non Final Office Action dated May 5, 2016", 14 pgs.
"U.S. Appl. No. 14/697,140, Response filed Jun. 13, 2016 to Non Final Office Action dated Apr. 8, 2016", 10 pgs.
"U.S. Appl. No. 13/833,567, Response filed Apr. 20, 2016 to Final Office Action dated Mar. 9, 2016", 10 pgs.
"European Application Serial No. 14716173.1, Response filed May 16, 2016 to Communication pursuant to Rules 161(1) and 162 EPC dated Nov. 5, 2015", 10 pgs.
"U.S. Appl. No. 13/288,459, Corrected Notice of Allowance dated Aug. 3, 2016", 4 pgs.
"U.S. Appl. No. 13/288,459, Corrected Notice of Allowance dated Sep. 9, 2016", 4 pgs.
"U.S. Appl. No. 13/288,459, Corrected Notice of Allowance dated Sep. 23, 2016", 4 pgs.
"U.S. Appl. No. 13/645,964, Notice of Allowance dated Jul. 21, 2016", 9 pgs.
"U.S. Appl. No. 13/751,846, Notice of Allowance dated Jul. 6, 2016", 9 pgs.
"U.S. Appl. No. 13/833,567, Notice of Allowance dated Sep. 27, 2016", 9 pgs.
"U.S. Appl. No. 13/833,567, Response filed Aug. 4, 2016 to Non Final Office Action dated May 27, 2016", 11 pgs.
"U.S. Appl. No. 13/838,755, Notice of Allowance dated Aug. 3, 2016", 8 pgs.
"U.S. Appl. No. 14/055,172, Non Final Office Action dated Jul. 14, 2016", 12 pgs.
"U.S. Appl. No. 14/055,191, Notice of Allowability dated Sep. 8, 2016", 7 pgs.
"U.S. Appl. No. 14/055,191, Notice of Allowance dated Aug. 31, 2016", 13 pgs.
"U.S. Appl. No. 14/055,191, Response filed Aug. 3, 2016 to Non Final Office Action dated May 16, 2016", 11 pgs.
"U.S. Appl. No. 14/094,311, Notice of Allowance dated Aug. 16, 2016", 12 pgs.
"U.S. Appl. No. 14/094,311, Response filed Jul. 26, 2016 to Restriction Requirement dated Jun. 22, 2016", 10 pgs.
"U.S. Appl. No. 14/095,614, Response filed Sep. 12, 2016 to Restriction Requirement dated Jul. 11, 2016", 11 pgs.
"U.S. Appl. No. 14/095,614, Restriction Requirement dated Jul. 11, 2016", 8 pgs.
"U.S. Appl. No. 14/095,639, Response filed Sep. 12, 2016 to Restriction Requirement dated Jul. 19, 2016", 7 pgs.
"U.S. Appl. No. 14/095,639, Restriction Requirement dated Jul. 19, 2016", 8 pgs.
"U.S. Appl. No. 14/107,350, Notice of Allowance dated Jul. 27, 2016", 7 pgs.
"U.S. Appl. No. 14/159,094, Non Final Office Action dated Jun. 29, 2016", 15 pgs.
"U.S. Appl. No. 14/159,094, Response filed Sep. 19, 2016 to Non Final Office Action dated Jun. 29, 2016", 13 pgs.
"U.S. Appl. No. 14/182,046, Non Final Office Action dated Jul. 15, 2016", 9 pgs.
"U.S. Appl. No. 14/182,046, Response filed Jun. 27, 2016 to Restriction Requirement dated Apr. 26, 2016", 7 pgs.
"U.S. Appl. No. 14/182,046, Response filed Oct. 17, 2016 to Non Final Office Action dated Jul. 15, 2016", 11 pgs.
"U.S. Appl. No. 14/211,977, Notice of Allowance dated Jul. 12, 2016", 9 pgs.
"U.S. Appl. No. 14/215,550, Non Final Office Action dated Jul. 19, 2016", 12 pgs.
"U.S. Appl. No. 14/275,548, Notice of Allowance dated Jul. 27, 2016", 7 pgs.

(56) References Cited

OTHER PUBLICATIONS

"U.S. Appl. No. 14/324,688, Corrected Notice of Allowance dated Sep. 22, 2016", 2 pgs.
"U.S. Appl. No. 14/456,286, Non Final Office Action dated Oct. 17, 2016", 17 pgs.
"U.S. Appl. No. 14/492,590, Notice of Allowance dated Oct. 5, 2016", 10 pgs.
"U.S. Appl. No. 14/492,590, Response filed Sep. 15, 2016 to Restriction Requirement dated Jul. 25, 2015", 7 pgs.
"U.S. Appl. No. 14/492,590, Restriction Requirement dated Jul. 25, 2016", 6 pgs.
"U.S. Appl. No. 14/492,590, Supplemental Response filed Sep. 26, 2016 to Restriction Requirement dated Jul. 25, 2016", 10 pgs.
"U.S. Appl. No. 14/589,191, Response filed Aug. 5, 2016 to Non Final Office Action dated May 5, 2016", 16 pgs.
"U.S. Appl. No. 14/697,140, Final Office Action dated Sep. 23, 2016", 10 pgs.
"U.S. Appl. No. 14/956,724, Supplemental Preliminary Amendment filed Oct. 3, 2016", 8 pgs.
"U.S. Appl. No. 15/278,777, Preliminary Amendment filed Oct. 3, 2016", 7 pgs.
"U.S. Appl. No. 15/297,844, Preliminary Amendment filed Oct. 20, 2016", 7 pgs.
"Chinese Application Serial No. 201480027708.4, Office Action dated May 26, 2016", W/ English Translation, 15 pgs.
"European Application Serial No. 12721676.0, Response filed Apr. 11, 2016 to Communication pursuant to Article 94(3) EPC dated Sep. 30, 2015", 38 pgs.
"European Application Serial No. 12791902.5, Response filed Feb. 23, 2016 to Examination Notification Art. 94(3) dated Aug. 14, 2015", 12 pgs.
"European Application Serial No. 12806211.4, Response filed Feb. 23, 2016 to Communication Pursuant to Article 94(3) EPC dated Aug. 13, 2015", 11 pgs.
"European Application Serial No. 12806211.4, Communication Pursuant to Article 94(3) EPC dated Jun. 23, 2016", 4 pgs.
"U.S. Appl. No. 13/281,009, Corrected Notice of Allowance dated Nov. 18, 2016", 4 pgs.
"U.S. Appl. No. 13/281,009, Corrected Notice of Allowance dated Dec. 12, 2016", 2 pgs.
"U.S. Appl. No. 13/281,009, Examiner Interview Summary dated Nov. 18, 2016", 2 pgs.
"U.S. Appl. No. 14/055,172, Final Office Action dated Dec. 22, 2016", 8 pgs.
"U.S. Appl. No. 14/055,172, Response filed Feb. 22, 2017 to Final Office Action dated Dec. 22, 2016", 11 pgs.
"U.S. Appl. No. 14/055,172, Response filed Nov. 14, 2016 to Non Final Office Action dated Jul. 14, 2016", 19 pgs.
"U.S. Appl. No. 14/094,311, Notice of Allowance dated Dec. 27, 2016", 8 pgs.
"U.S. Appl. No. 14/095,614, Non Final Office Action dated Jan. 19, 2017", 9 pgs.
"U.S. Appl. No. 14/095,614, Response filed Mar. 2, 2017 to Non Final Office Action dated Jan. 19, 2017", 14 pgs.
"U.S. Appl. No. 14/095,639, Non Final Office Action dated Jan. 18, 2017", 10 pgs.
"U.S. Appl. No. 14/095,639, Response filed Mar. 2, 2017 to Non Final Office Action dated Jan. 18, 2017", 9 pgs.
"U.S. Appl. No. 14/159,094, Examiner Interview Summary dated Nov. 29, 2016", 1 pg.
"U.S. Appl. No. 14/159,094, Notice of Allowance dated Nov. 29, 2016", Examiner Interview Summary from Nov. 29, 2016 included, 11 pgs.
"U.S. Appl. No. 14/182,046, Corrected Notice of Allowance dated Jan. 20, 2017", 6 pgs.
"U.S. Appl. No. 14/182,046, Notice of Allowance dated Dec. 8, 2016", 7 pgs.
"U.S. Appl. No. 14/215,550, Examiner Interview Summary dated Mar. 19, 2017", 3 pgs.
"U.S. Appl. No. 14/215,550, Final Office Action dated Feb. 1, 2017", 11 pgs.
"U.S. Appl. No. 14/215,550, Response filed Dec. 5, 2016 to Non Final Office Action dated Jul. 19, 2016", 13 pgs.
"U.S. Appl. No. 14/456,286, Notice of Allowance dated Feb. 15, 2017", 9 pgs.
"U.S. Appl. No. 14/456,286, Response filed Nov. 16, 2016 to Non Final Office Action dated Oct. 17, 2016", 9 pgs.
"U.S. Appl. No. 14/589,101, Advisory Action dated Feb. 21, 2017", 5 pgs.
"U.S. Appl. No. 14/589,101, Examiner Interview Summary dated Jan. 30, 2017", 3 pgs.
"U.S. Appl. No. 14/589,101, Final Office Action dated Nov. 16, 2016", 12 pgs.
"U.S. Appl. No. 14/589,101, Response filed Jan. 23, 2017 to Final Office Action dated Nov. 16, 2016", 9 pgs.
"U.S. Appl. No. 14/594,285, Non Final Office Action dated Jan. 11, 2017", 15 pgs.
"U.S. Appl. No. 14/594,285, Response filed Dec. 14, 2016 to Restriction Requirement dated Nov. 7, 2016", 8 pgs.
"U.S. Appl. No. 14/594,285, Restriction Requirement dated Nov. 7, 2016", 6 pgs.
"U.S. Appl. No. 14/697,140, Non Final Office Action dated Jan. 10, 2017", 12 pgs.
"U.S. Appl. No. 14/697,140, Response filed Mar. 1, 2017 to Non Final Office Action dated Jan. 10, 2017", 11 pgs.
"U.S. Appl. No. 14/697,140, Response filed Nov. 16, 2016 to Final Office Action dated Sep. 23, 2016", 13 pgs.
"U.S. Appl. No. 14/794,309, Non Final Office Action dated Nov. 22, 2016", 13 pgs.
"U.S. Appl. No. 14/794,309, Response filed Feb. 22, 2017 to Non Final Office Action dated Nov. 22, 2016", 12 pgs.
"U.S. Appl. No. 15/131,663, Preliminary Amendment filed Dec. 21, 2016", 6 pgs.
"U.S. Appl. No. 15/200,546, Preliminary Amendment filed Dec. 21, 2016", 6 pgs.
"U.S. Appl. No. 15/288,183, Preliminary Amendment filed Oct. 31, 2016", 7 pgs.
"U.S. Appl. No. 15/294,994, Preliminary Amendment filed Jan. 25, 2017", 8 pgs.
"U.S. Appl. No. 15/332,590, Preliminary Amendment filed Nov. 22, 2016", 5 pgs.
"U.S. Appl. No. 15/361,917, Preliminary Amendment filed Nov. 30, 2016", 6 pgs.
"U.S. Appl. No. 15/455,896, Preliminary Amendment filed Mar. 13, 2017", 6 pgs.
"Chinese Application Serial No. 201480027708.4, Office Action dated Feb. 14, 2017", With English Translation, 18 pgs.
"Chinese Application Serial No. 201480027708.4, Response filed Oct. 10, 2016 to Office Action dated May 26, 2016", With English Translation of Claims, 14 pgs.
"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique" brochure, Biomet® Sports Medicine. (2013) 16 pages.
Office Action dated Nov. 4, 2014 for U.S. Appl. No. 13/288,459, filed Nov. 3, 2011.
"ToggleLoc™ Fixation Device with ZipLoop™ Technology: ACL Reconstruction Bone-Tendon-Bone," by James R. Andrews, M.D., of Biomet Sports Medicine, a Biomet Company Brochure (2013), pp. 1-20.
International Preliminary Report on Patentability and Written Opinion dated May 30, 2014 for PCT/US2012/064832 which claims benefit of U.S. Appl. No. 13/295,126, filed Nov. 14, 2011.
International Search Report and Written Opinion dated Jun. 6, 2014 for PCT/US2014/026413 which claims benefit of U.S. Appl. No. 14/095,614, filed Dec. 3, 2013 and U.S. Appl. No. 14/095,639, filed Dec. 3, 2013.
ToggleLoc Fixation Device with ZipLoop Technology: Biceps Tendon Reattachment by Mark J. Albritton, M.D. and Daniel Worrel, M.D. of Biomet Sports Medicine, a Biomet Company Brochure (2099, 2011), pp. 1-12.

(56) References Cited

OTHER PUBLICATIONS

"AperFix® System Surgical Technique Guide. Single Tunnel Double Bundle.™" Cayenne Medical brochure. (Aug. 2008) 8 sheets.
"Arthroscopic Meniscal Repair using the Meniscal Cinch™", Surgical Technique brochure. (2008) Arthrex® 6 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Suture Tensioner w/Tensiometer," Arthrex®, Inc. catalog "Next Generation in Knee Ligament Reconstruction & Repair Technology," 2009.
"Technique for ACL Reconstruction with Acufex Director Drill Guide and Endobutton CL," by Thomas D. Roseberg, copyright 1999 Smith & Nephew.
"TriTis™ Tibial Fixation System and Implant" brochure. Scandius Biomedical (2006).
A. Weiler, et al; Biodegradierbare Interferenzschrauben in der Kreuzbandchirurgie; OP-Journal 14 pp. 278-284; (Mar. 1998).
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library. http://www.shoulder.com/bass_barber.html Printed May 19, 2005.
F. Alan Barber, M.D., "Using Sutures and Anchors," San Diego Shoulder Arthroscopy Course, 17th Annual Meeting. (Jun. 14, 2000).
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Preliminary Report on Patentability and Written Opinion dated Nov. 28, 2013 for PCT/US2012/037703, which claims benefit of U.S. Appl. No. 13/109,672, filed May 17, 2011,and U.S. Appl. No. 13/109,667, filed May 17, 2011.
International Preliminary Report on Patentability dated Dec. 6, 2012 for PCT/US2011/038188 claiming benefit of U.S. Appl. No. 12/788,966, filed May 27, 2010.
International Preliminary Report on Patentability dated Sep. 20, 2012 for PCT/US2011/026349 which claims benefit of U.S. Appl. No. 12/719,337, filed Mar. 8, 2010.
International Search Report and Written Opinion dated Feb. 6, 2013 for PCT/US2012/064832 which claims benefit of U.S. Appl. No. 13/295,126, filed Nov. 14, 2011.
International Search Report and Written Opinion dated Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion dated Mar. 6, 2013 for PCT/US2012/062738 which claims benefit of U.S. Appl. No. 13/288,459, filed Nov. 3, 2011.
International Search Report and Written Opinion dated Mar. 6, 2014 for PCT/US2013/075989 which claims benefit of U.S. Appl. No. 13/720,648, filed Dec. 19, 2012.
International Search Report and Written Opinion dated Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
International Search Report and Written Opinion dated Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.
Invitation to Pay Additional Fees dated Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees dated Jul. 19, 2012, for PCT/US2012/037703 claiming benefit of U.S. Appl. No. 13/109,667, filed May 7, 2011.
Invitation to Pay Additional Fees dated Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 (Oct. 2002): pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Pioneer® Sternal Cable System (2010).
Rapid Sternal Closure (2006) KLS Martin L.P. http://www.rapidsternalclosure.com/medical/demo.php Web accessed Sep. 8, 2008.
Roy Alan Majors, M.D.; "Meniscal repairs: proven techniques and current trends," Lippincott Williams & Wilkins, Inc.; 2002.
Saxena, Pankaj, MCh, DNB et al., "Use of Double Wires in Sternal Closure, A Useful Technique," Texas Heart® Institute. Journal List>Tex Heart Inst J > v.33(4); (2006).
Shoulder Arthroscopy; pp. H-2-H-22. (date unknown).
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Zeitani, Jacob, M.D., "A New Sternal Reinforcement Device to Prevent and Treat Sternal Dehiscence," CTSNet.org (Jun. 30, 2008).

* cited by examiner

METHOD AND APPARATUS FOR SOFT TISSUE FIXATION

CROSS-REFERENCE TO RELATED APPLICATIONS

This application is a divisional of U.S. patent application Ser. No. 13/098,927 filed on May 2, 2011, now U.S. Pat. No. 8,652,171 issued on Feb. 18, 2014, which is a continuation-in-part of U.S. patent application Ser. No. 12/196,398 filed on Aug. 22, 2008, now U.S. Pat. No. 7,959,650 issued on Jun. 14, 2011, which is a continuation-in-part of (a) U.S. patent application Ser. No. 11/541,506 filed on Sep. 29, 2006, now U.S. Pat. No. 7,601,165 issued on Oct. 13, 2009; (b) U.S. patent application Ser. No. 11/935,681 filed on Nov. 6, 2007, now U.S. Pat. No. 7,905,903 issued on Mar. 15, 2011; and (c) U.S. patent application Ser. No. 11/784,821 filed on Apr. 10, 2007.

This application is a divisional of U.S. patent application Ser. No. 13/098,927 filed on May 2, 2011, now U.S. Pat. No. 8,652,171 issued on Feb. 18, 2014, which is a continuation-in-part of U.S. patent application Ser. No. 12/938,902 filed on Nov. 3, 2010, now U.S. Pat. No. 8,597,327 issued on Dec. 3, 2013, which is a continuation-in-part of U.S. patent application Ser. No. 12/915,962 filed on Oct. 29, 2010, now U.S. Pat. No. 8,562,647 issued on Oct. 22, 2013, which is a continuation-in-part of U.S. patent application Ser. No. 12/719,337 filed on Mar. 8, 2010, which is a continuation-in-part of U.S. patent application Ser. No. 12/489,168 filed on Jun. 22, 2009, now U.S. Pat. No. 8,361,113 issued on Jan. 29, 2013, which is a continuation-in-part of U.S. patent application Ser. No. 12/474,802 filed on May 29, 2009, now U.S. Pat. No. 8,088,130 issued on Jan. 3, 2012, which is a continuation-in-part of (a) U.S. patent application Ser. No. 12/196,405 filed on Aug. 22, 2008, now U.S. Pat. No. 8,128,658 issued on Mar. 6, 2012; (b) U.S. patent application Ser. No. 12/196,407 filed on Aug. 22, 2008, now U.S. Pat. No. 8,137,382 issued on Mar. 20, 2012; (c) U.S. patent application Ser. No. 12/196,410 filed on Aug. 22, 2008, now U.S. Pat. No. 8,118,836 issued on Feb. 21, 2012; and (d) a continuation-in-part of U.S. patent application Ser. No. 11/541,506 filed on Sep. 29, 2006, now U.S. Pat. No. 7,601,165 issued on Oct. 13, 2009.

This application is a divisional of U.S. patent application Ser. No. 13/098,927 filed on May 2, 2011, now U.S. Pat. No. 8,652,171 issued on Feb. 18, 2014, which is a continuation-in-part of U.S. patent application Ser. No. 12/788,978 filed on May 27, 2010.

This application is a divisional of U.S. patent application Ser. No. 13/098,927 filed on May 2, 2011, now U.S. Pat. No. 8,652,171 issued on Feb. 18, 2014, which is a continuation-in-part of U.S. patent application Ser. No. 12/702,067 filed on Feb. 8, 2010, which is a continuation of U.S. patent application Ser. No. 11/541,505 filed on Sep. 29, 2006, now U.S. Pat. No. 7,658,751 issued on Feb. 9, 2010.

This application is a divisional of U.S. patent application Ser. No. 13/098,927 filed on May 2, 2011, now U.S. Pat. No. 8,652,171 issued on Feb. 18, 2014, which is a continuation-in-part of U.S. patent application Ser. No. 12/570,854 filed on Sep. 30, 2009, now U.S. Pat. No. 8,303,604 issued on Nov. 6, 2012, which is a continuation-in-part of: (a) U.S. patent application Ser. No. 12/489,181 filed on Jun. 22, 2009, now U.S. Pat. No. 8,298,262 issued on Oct. 30, 2012; (b) U.S. patent application Ser. No. 12/014,399 filed on Jan. 15, 2008, now U.S. Pat. No. 7,909,851 issued on Mar. 22, 2011, which is a continuation-in-part of U.S. patent application Ser. No. 11/347,661 filed on Feb. 3, 2006; now U.S. Pat. No. 7,749,250 issued on Jul. 6, 2010; and (c) U.S. patent application Ser. No. 12/014,340 filed on Jan. 15, 2008, now U.S. Pat. No. 7,905,904 issued on Mar. 15, 2011.

The entire disclosures of the aforementioned references are expressly incorporated herein by reference.

FIELD

The present disclosure relates to methods and apparatuses for securing soft tissue using a flexible suture construct and, more particularly, to flexible suture constructs including adjustable loops.

BACKGROUND

This section provides background information related to the present disclosure which is not necessarily prior art.

Surgical procedures are often performed on a body, for example, a human body or anatomy, to repair or replace various portions thereof. For example, the soft tissues of the body may need to be reattached to bones or a tear in the soft tissue may need repaired due to trauma, overuse, surgical intervention, or disease.

Soft tissues can be reattached to a bone or repaired using fastening devices such as screws, staples, and various types of suture anchors. Soft tissues are often fixed to various positions on the bone. For example, to replace a natural tendon fixation point or to replace the tendon itself, it may be desired to fix a graft to a selected bone area. One method of fixing a soft tissue to the selected area is to pass one end of a suture through a selected portion of the soft tissue to form a knot and fix another end of the suture to a selected area on the bone with a suture anchor. The present teachings provide surgical methods and apparatuses for improving engagement between a suture construct and a soft tissue.

SUMMARY

This section provides a general summary of the disclosure, and is not a comprehensive disclosure of its full scope or all of its features.

The present teachings provide surgical methods of attaching a first tissue to a second tissue. In one example, an exemplary method can include passing at least two adjustable loops through at least the first tissue to extend from an outer surface of the first tissue opposite a tissue engaging surface facing the second tissue, and attaching the two adjustable loops to a first selected area of the second tissue. The method can further include positioning a locking member within the two adjustable loops such that the locking member extends between the two adjustable loops adjacent the outer surface, engaging the locking member with the outer surface by drawing the two adjustable loops towards the outer surface, and compressing the first tissue between the locking member and the second tissue by tensioning the two adjustable loops.

In another example, the method can include attaching a suture anchor including a flexible construct to the second tissue, wherein the flexible construct extends from the suture anchor and includes at least two self-locking adjustable loops and tensioning members extending from the two adjustable loops. The method can further include passing the at least two self-locking adjustable loops and the tensioning members through the first tissue to extend from an outer surface of the first tissue opposite a tissue engaging surface facing the second tissue. The method can further include positioning an elongated locking member within the two self-locking adjustable loops such that the locking member extends between the two self-locking adjustable loops adjacent the outer surface. The method can further include cinching the two self-locking adjustable loops around the locking member by selectively pulling on the tensioning members, engaging the locking member with the outer surface of the first tissue, and compressing the first tissue between the locking member and the second tissue by selectively pulling on the tensioning members.

In another example, the method can include attaching a self-locking, first adjustable loop to a first anchor at a first end of the first adjustable loop and a second anchor at a second end of the first adjustable loop, wherein the first adjustable loop includes a first tensioning member. The method can further include attaching a self-locking, second adjustable loop to a third anchor at a first end of the second adjustable loop and a fourth anchor at a second end of the second adjustable loop, wherein the second adjustable loop includes a second tensioning member. The method can further include passing the first ends of the first and second adjustable loops through separate apertures in the first tissue to extend from an outer surface of the first tissue opposite a tissue engaging surface facing the second tissue. The method can further include attaching the first and third anchors to the second tissue in a first selected area overlapping the first tissue, and attaching the second and fourth anchors to the second tissue in a second selected area spaced apart from the first selected area. The method can further include positioning a locking member between the outer surface and the first and second adjustable loops, and engaging the first and second adjustable loops with the locking member by pulling on the first and second tensioning members. The method can further include engaging the locking member with the outer surface of the first tissue, and compressing the first tissue between the locking member and the second tissue by pulling on the first and second tensioning members. The second selected area can be disposed adjacent an end of the first tissue.

The present teachings also provide tissue fixation apparatuses that can be used to attach a first tissue to a second tissue. In one example, an exemplary tissue fixation apparatus can include a flexible construct and an elongated locking member. The flexible construct can include at least two adjustable loops, tensioning members, and an anchor. The two adjustable loops can be configured to pass through the first tissue, and to be spaced apart along an outer surface of the first tissue in a first direction. The tensioning members can extend from the two adjustable loops, and can be configured to reduce the two adjustable loops from a first size to a second size. The anchor can be configured to attach the flexible construct to the second tissue in a first selected area of the second tissue. The locking member can be configured to be received within the two adjustable loops at the first size, and to engage the two adjustable loops at the second size.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
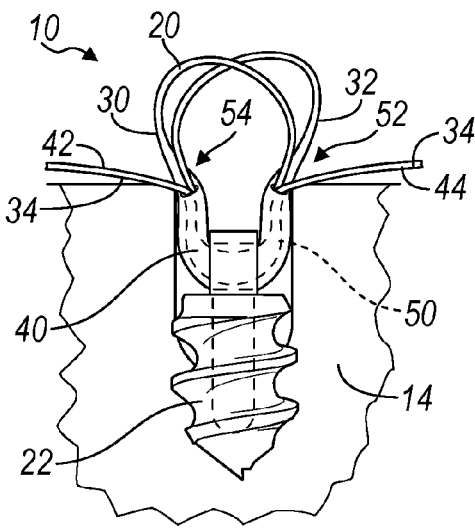
FIGS. 1-3 are fragmentary side views illustrating an exemplary tissue fixation device and method for affixing two tissues together using the tissue fixation device according to the present teachings.
Figure 2:
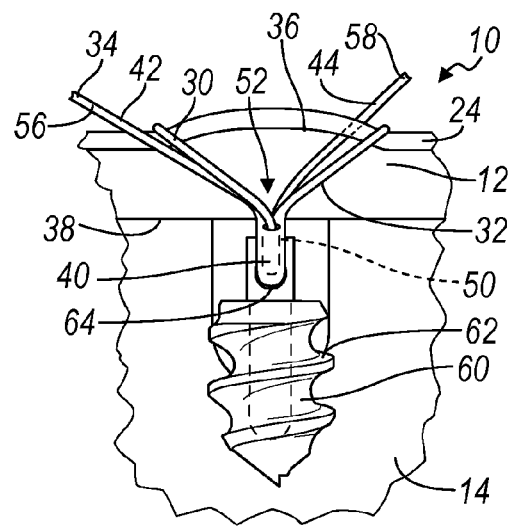
Figure 3:
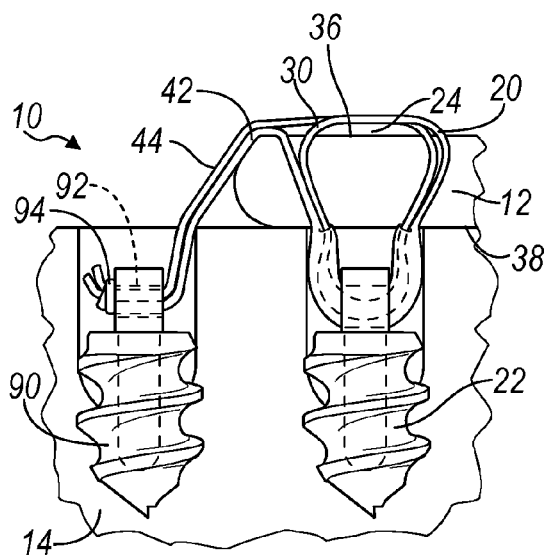

With particular reference to FIGS. 1-3, an exemplary tissue fixation device (TFD) 10 for affixing a first tissue 12 to a second tissue 14 is shown. The first tissue 12 and the second tissue 14 can be independently selected from soft tissue or bone to provide any one of a soft tissue-to-bone, a soft tissue-to-soft tissue, or a bone-to-bone connection. For purposes of the example shown in FIGS. 1-3, a soft tissue-to-bone connection is described. Various components of the TFD 10 are described first and then various surgical methods for affixing the first tissue 12 to the second tissue 14 using the TFD 10 are described.

Generally, the TFD 10 can be composed of various biocompatible materials, including bioresorbable and non-bioresorbable materials. The TFD 10 can include a flexible suture construct 20, a suture anchoring member 22, and a locking member 24. Generally, the suture construct 20 can be formed of a monofilament, a braided fiber or strand, or other flexible member or suture used to affix the tissues 12, 14. The suture construct 20 can include at least two adjustable loops 30, 32 and at least one tensioning member 34. In various implementations, as illustrated by the examples discussed below, a tensioning member 34 may be provided for each of the loops 30, 32. Additionally, the loops 30, 32 and the tensioning member or members 34 can be formed from a single suture construct.

Together, the loops 30, 32 and the tensioning member or members 34 can cooperate to cinch the loops 30, 32 and to create tension in the suture construct 20. In this way, the loops 30, 32 and the tensioning member or members 34 can cooperate to draw and/or compress the tissues 12, 14 together. The loops 30, 32 can be adapted to both receive and engage the locking member 24. In various implementations, the loops 30, 32 can be self-locking adjustable loops, as illustrated by the examples discussed below. Together, the loops 30, 32 and the locking member 24 can cooperate to engage a major or outer surface 36 of the first tissue 12 opposite a tissue engaging surface 38 to be engaged with the second tissue 14. The tensioning member or members 34 can be configured to adjust the suture construct 20 between an untensioned state and a tensioned state.

The loops 30, 32, the tensioning member or members 34, and/or the suture anchoring member 22 can be created using various surgical methods and suture constructs. For example, whip and/or mattress stitching methods employing a suture thread can be used. As another example, self-locking adjustable loop suture constructs can be employed. Exemplary self-locking adjustable loop suture constructs are disclosed in commonly assigned U.S. Pat. No. 7,658,751 and U.S. Pat. No. 7,601,165, the entire disclosures of which are expressly incorporated herein by reference.

According to the example shown in FIGS. 1-3, the suture construct 20 can include a braided body 40 and tensioning strands 42, 44 that form self-locking adjustable loops 30, 32 and separate tensioning members 34 for each of the loops 30, 32. The braided body 40 and the tensioning strands 42, 44 can be formed in a single suture construct using a braiding process for braiding fibers composed of a biocompatible material. The braided body 40 can define a longitudinal passage 50 and apertures 52, 54 longitudinally spaced along and in communication with the longitudinal passage 50. The apertures 52, 54 can be created during the braiding process as loose portions between pairs of fibers. The tensioning strands 42, 44 can be created using one or more of the fibers used to create the braided body. In this way, the tensioning strands 42, 44 can be integral to the braided body 40.

An end 56 of the tensioning strand 42 can be inserted through the aperture 52 and passed through the longitudinal passage 50 and out the aperture 54 to create the loop 30. Similarly, an end 58 of the tensioning strand 44 can be inserted through the aperture 54 and passed through the longitudinal passage 50 and out the aperture 52 to create the loop 32. Sizes or diameters of the loops 30, 32 can be adjusted by retracting or advancing the tensioning strands 42, 44, respectively, within the longitudinal passage 50.

The suture anchoring member 22 can be configured to affix the suture construct 20 to the second tissue 14. In various implementations, the suture anchoring member 22 can be created by the suture construct 20 alone, or in combination with, a separate component. According to the example shown in FIGS. 1-3, the suture anchoring member 22 can be a separate fastener or suture anchor 60 including external threads 62 configured to threadingly engage the second tissue 14 and an eyelet 64 configured to receive the braided body 40. It should be understood that the suture anchor 60 is merely exemplary in nature, and that other suture anchors can be used. For example, threaded or non-threaded suture anchors can be used. The suture anchor 60 can be composed of various bioresorbable materials such as, for example, the LactoSorb® material available from Biomet Sports Medicine, LLC of Warsaw, Ind. Alternately, or additionally, the suture anchor may be composed of other non-bioresorbable materials, such as, for example, titanium-based materials. Various bioresorbable and non-bioresorbable, soft and hard suture anchors are available from, for example, Biomet Sports Medicine, LLC of Warsaw, Ind.

The locking member 24 can be an elongated member that is received within each of the loops 30, 32, and that spans a lateral distance between the loops 30, 32. The locking member 24 can be further configured to engage and thereby restrain the loops 30, 32 from pulling through the first tissue 12 and to maintain the lateral distance between the loops 30, 32, when the suture construct 20 is in the tensioned state. For example, the locking member 24 can be constructed to have a predetermined strength for a period after implantation for resisting pull through by the loops 30, 32. The locking member 24 can be further sized to provide a predetermined bearing surface for distributing compressive loads to the first tissue 12 generated by the suture construct 20 in the tensioned state. More specifically, the locking member 24 can transmit compressive loads received from the loops 30, 32 to the first tissue 12.

Generally, the locking member 24 can be composed of various bioresorbable or non-bioresorbable materials. The locking member 24 can include flexible and/or semi-rigid sections that enable the locking member 24 to conform to the outer surface 36 of the first tissue 12, yet distribute the compressive loads to the first tissue 12 in a predetermined manner. According to the example shown in FIGS. 1-3, the locking member 24 can be a length of a flexible strip of surgical fabric such as, for example, surgical tape. The surgical tape can include braided fibers. The locking member 24 can be cut to a predetermined length and/or cut to a custom length during a surgical procedure based on a particular patient.

Figure 4:
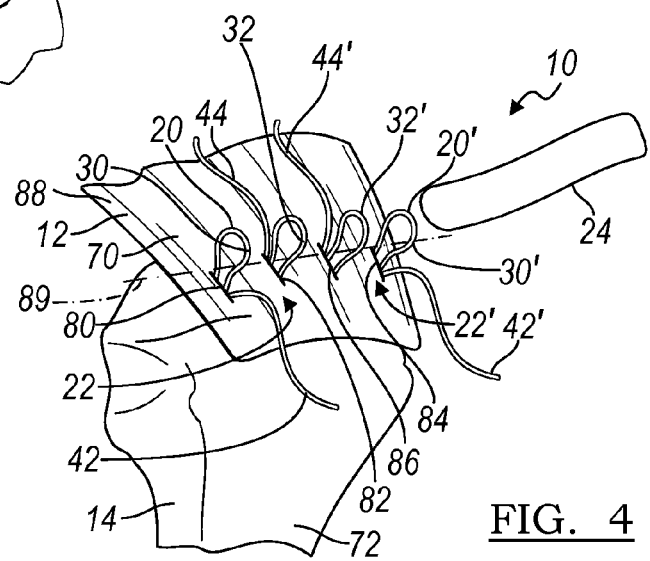
FIGS. 4-6 are fragmentary environmental perspective views illustrating an exemplary method of using the tissue fixation device shown in FIGS. 1-3 to affix a rotator cuff to a humerus.
Figure 5:
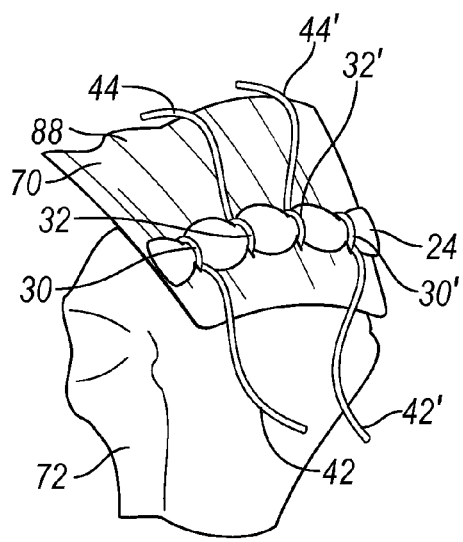
Figure 6:
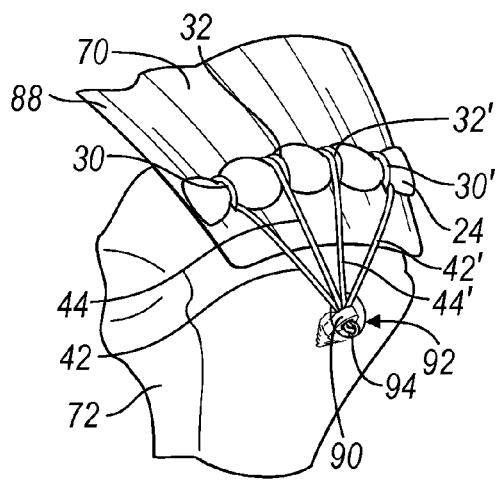

With additional reference to FIGS. 4-6, an exemplary surgical method for affixing the tissues 12, 14 together using the TFD 10 according to the present teachings will now be described. For exemplary purposes, the method includes affixing a rotator cuff 70 to a humerus 72. In various implementations, the TFD 10 and the corresponding method can include two or more suture constructs, such as the suture construct 20, with a single locking member, such as the locking member 24. As illustrated in FIGS. 4-6, the TFD 10 can further include a second suture construct 20' substantially similar to the suture construct 20. The second suture construct 20' can be coupled to the second tissue 14 via a second suture anchoring member 22' substantially similar to the suture anchoring member 22. For purposes of the following description, corresponding reference numerals are used to indicate corresponding parts of the suture constructs 20, 20' throughout the several views of the drawings.

With continued reference to FIGS. 1-6, the method can include preparing the humerus 72 to receive suture anchoring members 22, 22' in a selected area where the rotator cuff 70 is to be attached. The humerus 72 can be prepared by creating threaded holes in the humerus 72 in selected areas, each at a desired angle of insertion. The threaded holes can be created to a depth that enables the suture anchoring members 22, 22' and/or portions of the suture constructs 20, 20' to be located beneath an outer surface of the humerus 72.

Next, suture constructs 20, 20' can be coupled to the humerus 72 via the suture anchoring members 22, 22', respectively. The suture constructs 20, 20' can be coupled to the suture anchoring members 22, 22' prior to, at the same time, or after securing the suture anchoring members 22, 22' to the humerus 72. According to the examples shown in FIGS. 1-6, the suture construct 20 can be coupled to the suture anchoring member 22 prior to threadingly engaging the suture anchoring member 22 with the humerus 72. More particularly, tensioning strand 42 can be inserted through the eyelet 64 until the braided body 40 is approximately centered within the eyelet 64. Next, the tensioning strands 42, 44 can be passed through the longitudinal passage 50 to create the loops 30, 32 as discussed above. The suture construct 20' can be coupled to the suture anchoring member 22' and subsequently to the tissue 14 in a similar manner.

Next, with particular reference to FIG. 4, the loops 30, 32 and tensioning strands 42, 44 can be passed through incisions or apertures 80, 82 formed into the rotator cuff 70. Similarly, the loops 30', 32' and tensioning strands 42', 44' can be passed through apertures 84, 86 of the rotator cuff 70. The apertures 80, 82, 84, 86 can be spaced apart and can extend generally parallel to one another as shown. In various implementations, one or more of the tensioning strands 42, 44, 42', 44' can be passed between the tissues 12, 14, rather than through the corresponding apertures 80, 82, 84, 86. The apertures 80, 82, 84, 86 can be created prior to or at the same time as the passing of the corresponding loops 30, 32, 30', 32' and the tensioning strands 42, 44, 42', 44'. The loops 30, 32, 30', 32' and tensioning strands 42, 44, 42', 44' can be passed using a separate needle or other suitable suture passer or device. For example, suitable devices include devices sold under the trade names "BiPass™", SpeedPass™", and "ArthroPass™", all made by Biomet Sports Medicine, LLC of Warsaw, Ind.

The loops 30, 32, 30', 32' can be passed such that distal ends of the loops 30, 32, 30', 32' are spaced apart along a major or outer surface 88 of the rotator cuff 70. The loops 30, 32, 30', 32' can be spaced apart along a line or axis 89 to face or open towards each other as shown. The loops 30, 32, 30', 32' can be spaced apart to span a selected area of the rotator cuff 70 to be attached to the humerus 72. The tensioning strands 42, 44, 42', 44' can be passed through the same apertures 80, 82, 84, 86 as the corresponding loops 30, 32, 30', 32' as shown, or through separate, spaced apertures as discussed in further detail below. Next, as shown between FIGS. 4-5, the locking member 24 can be passed through and positioned within each of the loops 30, 32, 30', 32'. Sizes or diameters of the loops 30, 32, 30', 32' can be adjusted to enable the locking member 24 to be passed through the loops 30, 32, 30', 32'. The diameters can be adjusted as discussed above prior to or when positioning the locking member 24.

With the locking member 24 thus positioned, the tensioning strands 42, 44, 42', 44' can be selectively pulled to cinch the loops 30, 32, 30', 32' around the locking member 24 and to draw the locking member 24 into engagement with the rotator cuff 70. With the locking member 24 engaged, the tensioning strands 42, 44, 42', 44' can be further pulled to further close and tension the loops 30, 32, 30', 32' and draw the locking member 24 towards the suture anchoring members 22, 22'. Further drawing the locking member 24 can draw the rotator cuff 70 in close proximity with the humerus 72 and subsequently compress the rotator cuff 70, thereby creating tension in the suture constructs 20, 20'. More specifically, the rotator cuff 70 can be drawn into a desired relationship with the humerus 72. FIGS. 1 and 4 illustrate the suture constructs 20, 20' in an untensioned state. FIGS. 2, 3, and 5 illustrate the suture constructs 20, 20' in a tensioned state.

Tension in the loops 30, 32, 30', 32' can be retained by the self-locking features of the constructs 20, 20' without continuing to pull on the tensioning strands 42, 44, 42', 44'. Although not specifically shown, with the rotator cuff 70 and the humerus 72 in the desired relationship, one or more of the tensioning strands 42, 44, 42', 44' can be cut to a desired length, for example, flush to the outer surface 88. In this way, excess length can be removed. Alternately, the tensioning strands 42, 44, 42', 44' can be drawn past an end of the rotator cuff 70 and attached to a selected area of the humerus 72 as shown in FIG. 6. More particularly, the tensioning strands 42, 44, 42', 44' can be drawn and attached so as to extend in a direction generally parallel to a direction in which the rotator cuff 70 contracts during muscle action. Tensioning strands 44, 44' can be drawn around the locking member 24 and positioned to adjoin the loops 32, 32', respectively, as shown.

The tensioning strands 42, 44, 42', 44' can be attached using another suture anchoring member 90 substantially similar to the suture anchoring member 22. The tensioning strands 42, 44, 42', 44' can be coupled to the suture anchoring member 90 by passing the tensioning strands 42, 44, 42', 44' through an eyelet 92 of the suture anchoring member 90 and creating a knot 94. The humerus 72 can be prepared to receive the suture anchoring member 90 in substantially the same manner as the suture anchoring members 22, 22'.

Figure 7:
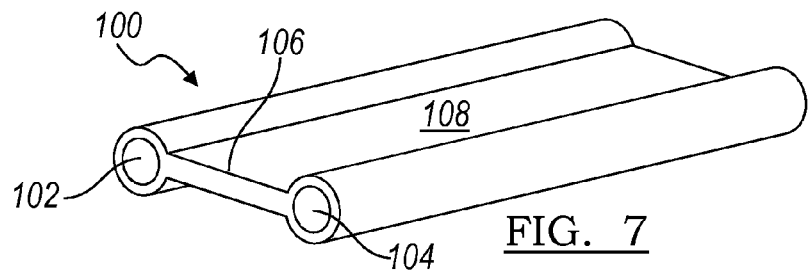
FIG. 7 is a perspective view illustrating an exemplary locking member according to the present teachings.
Figure 8:
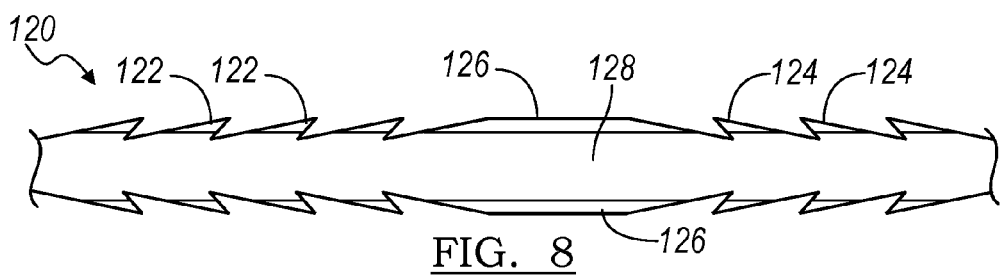
FIG. 8 is a fragmentary top view illustrating another exemplary locking member according to the present teachings.
Figure 9:
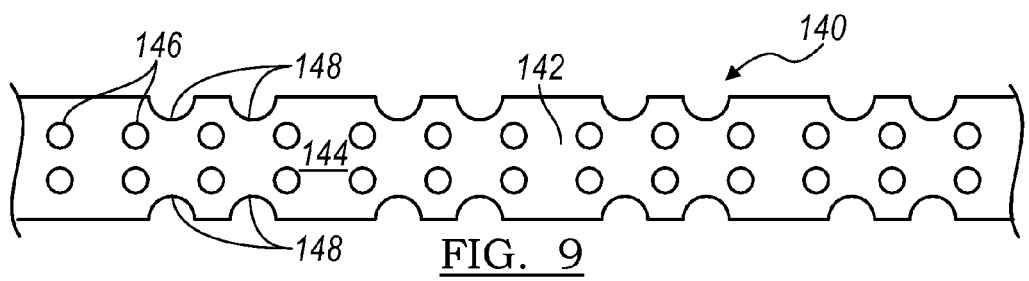
FIG. 9 is a fragmentary top view illustrating another exemplary locking member according to the present teachings.

With particular reference to FIGS. 7-14, various other exemplary configurations of the locking member 24 according to the present teachings are shown. FIGS. 7-9 illustrate various flexible, elongated, and generally thin, flat configurations that can be cut to a desired length and/or width from a larger stock of material prior to and/or during a surgical procedure. With particular reference to FIG. 7, an exemplary locking member 100 can include monofilament fibers 102, 104 connected along a length by a fabric of intertwined threads, or braided fabric 106. The monofilament fibers 102, 104 can have diameters greater than a thickness of the braided fabric 106. The braided fabric 106 can circumscribe the monofilament fibers 102, 104 and include a central section 108 that spans a width between the monofilament fibers 102, 104. The locking member 100 can be oriented between adjacent loops (e.g., loops 30, 32) of a suture construct so that the monofilament fibers 102, 104 span a distance between the loops. Alternately, the locking member 100 can be oriented so that the central section 108 spans the distance between the loops and the larger side sections created by the monofilament fibers 102, 104 engage opposite sides of the loops. In this way, the monofilament fibers 102, 104 can provide a loop engaging feature for fixing ends of the locking member 100 relative to the loops and/or for fixing the distance between the loops.

Referring now to FIG. 8, another exemplary locking member 120 can include outwardly extending edges or protrusions 122, 124 that create peripheral recesses along a length that are configured to engage two or more loops (e.g., loops 30, 32) of a suture construct. At least two protrusions 122, 124 can be provided to fixedly position the loops and thereby maintain a distance between the loops when the loops are engaged. The protrusions 122, 124 can extend at an angle, for example towards each other, to create barbs or hooks as shown for engaging and securely holding the loops at a separated distance. In an exemplary construction, the locking member 120 can include monofilament fibers 126 connected along a length by a braided fabric 128 in a substantially similar way as the locking member 100. The protrusions 122, 124 can be created using various methods. For example, the protrusions 122, 124 can be created during the braiding process used to create the braided fabric 128. As another example, a cutting process, for example a die cutting process, can be used to create the protrusions 122, 124.

Referring now to FIG. 9, another exemplary locking member 140 can include a length or strip of a non-woven bio-textile 142, such as, for example, the Scaftex® materials offered by Biomedical Structures of Warwick, R.I. Non-woven bio-textiles can be manufactured from a variety of synthetic, absorbable polymeric fibers, including polyglycolic acid (PGA), poly-L-lactide (PLLA), poly DL-lactide-co-glycolide acid (PLGA), blends, and other fibers. The bio-textile 142 can include first regions 144 having a higher density than second regions 146. The first and second regions 144, 146 can have a predetermined and regular arrangement with respect to a broad or major surface of the locking member 140 configured to engage loops of a suture construct. The bio-textile 142 can be die cut from a sheet to include peripheral depressions 148 along opposite sides configured to engage the loops of the suture construct. The peripheral depressions 148 can adjoin the higher density first regions 144. In this way, the loops can engage and be retained in higher density regions specifically suited to restrain the loops from pulling through the adjoining tissue.

FIGS. 10-14 illustrate various adjustable locking members according to the present teachings. Generally, the locking members are flexible and elongate configurations created using various adjustable loop constructions. The adjustable loop constructions can enable adjustments to sizes or diameters of one or more loop sections and an overall length of the locking members prior to and during a surgical procedure. The adjustments can further enable loop engaging members at opposite ends of the locking members to be brought into engagement with one or more loops of a suture construct. The loop engaging members can be deformable between a first configuration when the locking members are untensioned and/or unengaged with loops of a suture construct and a second configuration facilitating engagement between the locking members and the loops. Additional suitable adjustable loop constructions are disclosed in commonly assigned U.S. patent application Ser. No. 11/541,506, the entire disclosure of which is expressly incorporated herein by reference.

Figure 10:
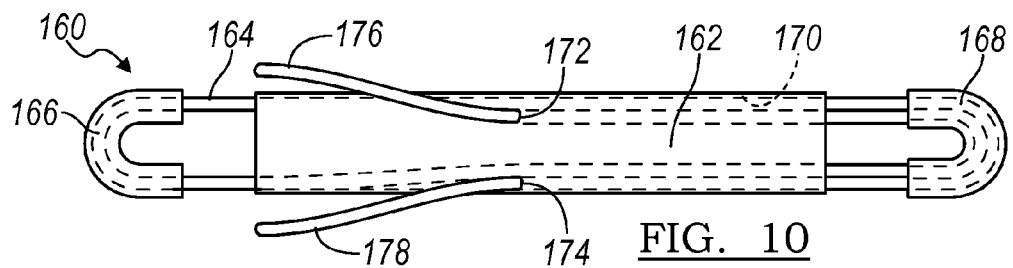
FIG. 10 is a top view illustrating an exemplary adjustable locking member according to the present teachings.

With particular reference to FIG. 10, an exemplary adjustable locking member 160 can include an adjustable loop construct including a sleeve 162, a fiber or strand 164, and sleeves 166, 168. The sleeve 162 can have a braided construction and can define a longitudinal passage 170 and apertures 172, 174. The strand 164 can be wrapped into a single loop or coil passing through the longitudinal passage 170 and the sleeves 166, 168 as shown to create adjustable loop sections that extend from opposite ends of the sleeve 162. Ends 176, 178 of the strand 164 can pass through the apertures 172, 174 and can be used as tensioning members used to adjust sizes or diameters of the adjustable loop sections and thereby adjust an overall length of the locking member 160 or, more specifically, a distance between the sleeves 166, 168. The sleeves 166, 168 can have a braided construction similar to the sleeve 162 and can function as loop engaging members.

Figure 11:
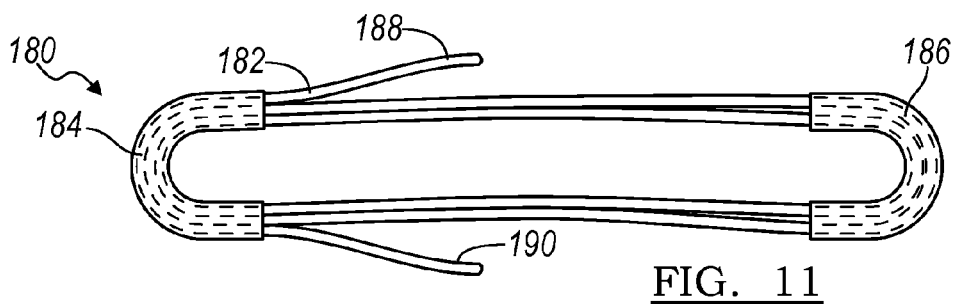
FIG. 11 is a top view illustrating another exemplary adjustable locking member according to the present teachings.

Referring now to FIG. 11, another exemplary adjustable locking member 180 can include an adjustable loop construct including a fiber or strand 182 and sleeves 184, 186. The strand 182 can be wrapped into a single loop or coil passing through the sleeves 184, 186 as shown to create an adjustable closed loop configuration. Ends 188, 190 of the strand 182 can extend through the sleeves 184, 186 and exit at opposite ends of the sleeve 184. A size or diameter of the loop or coil and an overall distance between the sleeves 184, 186 can be adjusted by pulling on one or both the first and second ends 188, 190. The sleeves 184, 186 can include flexible sections to facilitate adjustments and/or semi-rigid sections to maintain a predetermined curvature or diameter of the sleeves 184, 186 after the adjustments. The sleeves 184, 186 can also function as loop engaging members deformable between a first configuration and a second configuration. The first configuration can be a first shape configured to maintain an overall shape of the locking member 180 prior to engaging the locking member 180 with loops of a suture construct, for example, the shape shown in FIG. 11. The second configuration can be a second shape different from the first shape configured to facilitate engagement between the locking member 180 and the loops of the suture construct, for example, the cinched shape shown in FIG. 16 and discussed below.

Figure 12:
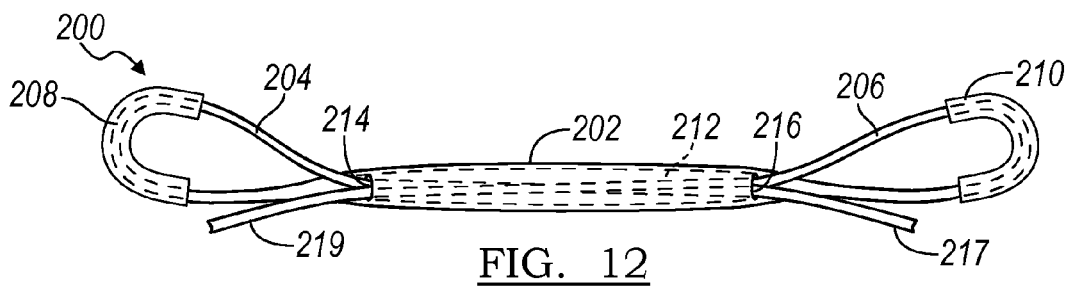
FIG. 12 is a top view illustrating another exemplary adjustable locking member according to the present teachings.

Referring now to FIG. 12, another exemplary adjustable locking member 200 can include a self-locking adjustable loop construct formed from a braided suture construct. The locking member 200 can include a braided body 202, fibers or strands 204, 206, and sleeves 208, 210. The braided body 204 can have a longitudinal passage 212 and apertures 214, 216. The longitudinal passage 212 and the apertures 214, 216 can be sized relative to the strands 204, 206 to provide the self locking feature. A first end 217 of the strand 204 can be passed through the sleeve 208, then through the aperture 214 and the longitudinal passage 212 and out the aperture 216 to create a first self-locking adjustable loop at one end of the adjustable locking member 200. A second end 219 of the strand 206 can be passed through the sleeve 210, then through the aperture 216 and the longitudinal passage 212 and out the aperture 214 to create a second self-locking adjustable loop at an opposite end.

The apertures 214, 216 can be loose portions between pairs of fibers forming the braided body 204. While two apertures 214, 216 are shown, additional apertures can be provided so that each of the strands 204, 206 can be passed through separate apertures to create the adjustable loops. Sizes or diameters of the adjustable loops can be separately adjusted by selectively pulling on the first and second ends 217, 219. By adjusting the diameter of one or both of the loops, an overall length of the adjustable locking member 200 and, more particularly, a distance between the sleeves 208, 210 can be adjusted.

Figure 13:
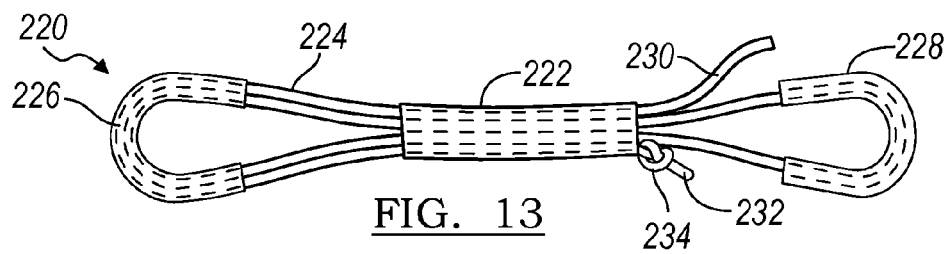
FIG. 13 is a top view illustrating another exemplary adjustable locking member according to the present teachings.

Referring now to FIG. 13, another exemplary adjustable locking member 220 can include an adjustable loop construct including a tubular body 222, a fiber or strand 224, and sleeves 226, 228. The strand 224 can be wound in a single loop or coil passing through the tubular body 222 and the sleeves 226, 228, as shown, to create two adjustable loop sections extending from opposite ends of the tubular body 222. First and second ends 230, 232 of the strand 224 can pass through the tubular body 222 to exit at one of the opposite ends. The first end 230 can be a free end that functions as a tensioning member that can be pulled to simultaneously adjust sizes or diameters of the adjustable loop sections and thereby adjust a distance between the sleeves 226, 228. The second end 232 can be tied in a knot 234 that engages the tubular body 222 to prevent the second end 232 from pulling through the tubular body 222 when making adjustments.

Figure 14:
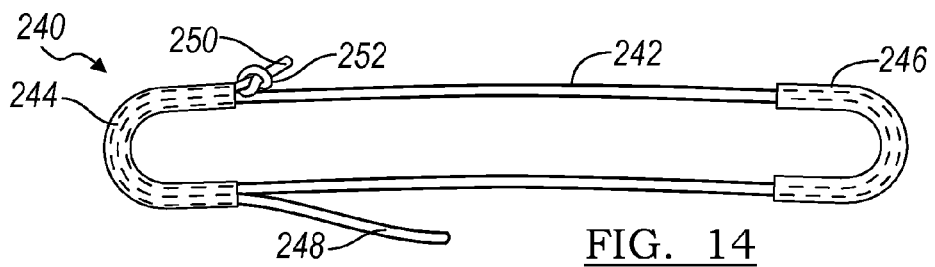
FIG. 14 is a top view illustrating another exemplary adjustable locking member according to the present teachings.

Referring now to FIG. 14, another exemplary adjustable locking member 240 can include an adjustable loop construct including a fiber or strand 242 and sleeves 244, 246. The strand 242 can be wound into a single loop or coil passing through the sleeves 244, 246, as shown, to create an adjustable closed loop configuration similar to that of the locking member 180 discussed above. First and second ends 248, 250 can exit opposite ends of the sleeve 244. The first end 248 can be a free end that functions as a tensioning member. The second end 250 can be tied in a knot 252 that engages the sleeve 244 to prevent the second end 250 from pulling through the sleeve 244 when pulling on the first end 248 to make adjustments.

Figure 15:
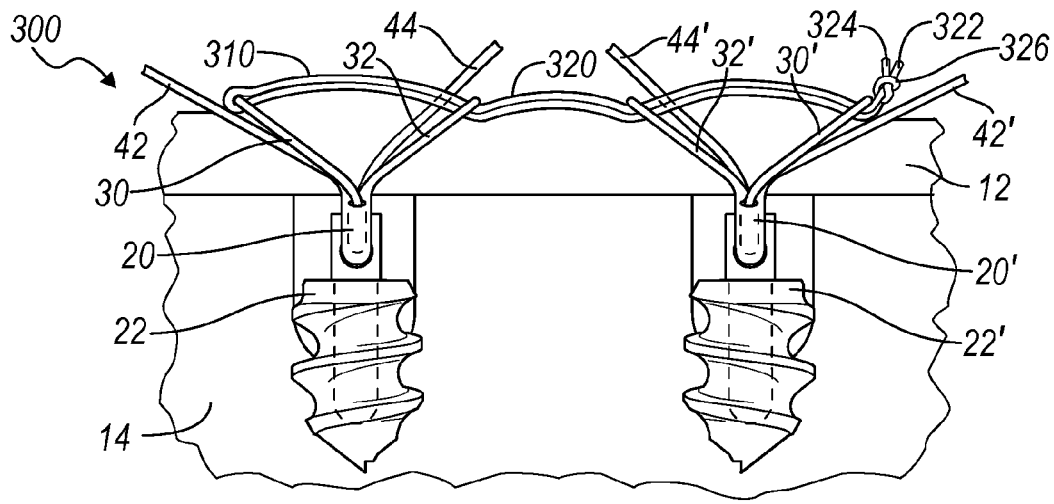
FIG. 15 is a fragmentary side view illustrating an exemplary method for coupling a locking member to a flexible suture construct according to the present teachings.

With particular reference to FIG. 15, another TFD 300 and surgical method for using the TFD 300 for affixing the first tissue 12 to the second tissue 14 is shown. The TFD 300 and the method illustrate alternate features that can be employed to engage a locking member with two or more loops of a suture construct, according to the present teachings. For exemplary purposes, the TFD 300 can include the suture constructs 20, 20' and the suture anchoring members 22, 22'. The TFD 300 can further include a locking member 310. The locking member 310 can incorporate one or more features of the locking members 24, 100, 120, 140, 160, 180, 200, 220, 240 discussed above. According to the example shown in FIG. 15, the locking member 310 can be a fiber or strand 320 having first and second ends 322, 324.

With continued reference to FIG. 15, an exemplary method of using the TFD 300 can include coupling the suture constructs 20, 20' to the second tissue 14 and passing the loops 30, 32, 30', 32' through the first tissue 12 in substantially the same manner as described above for the TFD 10. Next, with the suture constructs 20, 20' in an untensioned state, the first end 322 can be passed through a first end loop, for example, the loop 30', and then successively through the remaining loops 32', 32, 30 in that order. Next, the strand 320 can be wrapped around a second end loop, here, the loop 30, by pulling the first end 322 back towards the adjacent loop 32. Next, the first end 322 can be successively passed back through the loops 32, 32', 30' in that order.

Once the strand 320 is routed through the loops 30, 32, 30', 32' in the foregoing manner, the tensioning strands 42, 44, 42', 44' can be selectively pulled to cinch the loops 30, 32, 30', 32' around the strand 320 and to draw the strand 320 into engagement with the first tissue 12. With the strand 320 engaged, a distance between the loops 30, 30' can be adjusted by manipulating (e.g., pulling) one or both the first and second ends 322, 324. Next, the first and second ends 322, 324 can be secured together using a knot 326 that functions as a loop engaging member that engages the loop 30' and thereby inhibits the loops 30, 30' from separating during subsequent steps.

Next, the tensioning strands 42, 44, 42', 44' can be further selectively pulled to draw the loops 30, 32, 30', 32' and the strand 320 towards the suture anchoring members 22, 22'. Further drawing the loops 30, 32, 30', 32' can draw the first tissue 12 in close proximity with the second tissue 14 in a desired relationship, and subsequently compress the first tissue 12, thereby creating tension in the suture constructs 20, 20'. FIG. 15 illustrates the suture constructs 20, 20' in a tensioned state. With the first and second tissues in the desired relationship, the tensioning strands 42, 44, 42', 44' can be drawn under tension and attached to a selected area of the second tissue 14 in any suitable manner. For example, the tensioning strands 42, 44, 42', 44' can be attached in a manner substantially similar to that described above for the TFD 10.

Figure 16:
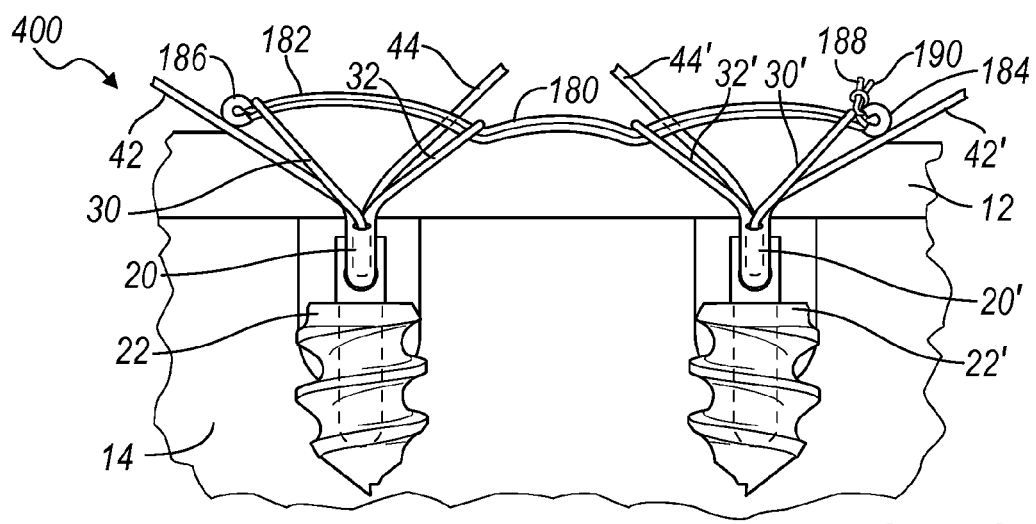
FIG. 16 is a fragmentary side view illustrating another exemplary method for coupling a locking member to a flexible suture construct according to the present teachings.

With particular reference to FIG. 16, another TFD 400 and surgical method for using the TFD 400 for affixing the first tissue 12 to the second tissue 14 will now be described. The TFD 400 and the method illustrate alternate features according to the present teachings that can be employed to engage loop engaging members of an adjustable locking member with two or more loops of a suture construct. For purposes of the example shown in FIG. 16, the locking member 180 shown in FIG. 11 can be employed in the TFD 400. The TFD 400 can include the suture constructs 20, 20' and the suture anchoring members 22, 22'.

With reference to FIG. 11 and FIG. 16, an exemplary method of using the TFD 400 can include coupling the suture constructs 20, 20' to the second tissue 14 and passing the loops 30, 32, 30', 32' through the first tissue 12 in substantially the same manner as described above for the TFD 10. Next, with the TFD 400 in an untensioned state, the locking member 180 can be passed through and positioned within the loops 30, 32, 30', 32' such that ends of the locking member 180 extend past the end loops 30, 30'. More particularly, the locking member 180 can be positioned such that the sleeves 184, 186 are disposed outboard of the end loops 30, 30'.

Once the locking member 180 is routed through the loops 30, 32, 30', 32' in the foregoing manner, the tensioning strands 42, 44, 42', 44' can be selectively pulled to cinch the loops 30, 32, 30', 32' around the locking member 180 and to draw the locking member 180 into engagement with the first tissue 12. With the locking member 180 engaged, the sleeves 184, 186 can be brought into engagement with the loops 30, 30', respectively, by pulling on one or both the ends 188, 190. The sleeves 184, 186 can deform from a first configuration having a first shape (see FIG. 11) to a second configuration having a cinched shape as shown in FIG. 16 that resists pull through. Once the sleeves 184, 186 are engaged, a distance between the loops 30, 30' can be reduced by further pulling on one or both of the ends 188, 190. Next, the first and second ends 188, 190 can be tied together to create the knot 326 that engages the sleeve 184 and thereby fixes the length of the locking member 180 and the distance between the loops 30, 30'.

Next, the tensioning strands 42, 44, 42', 44' can be further selectively pulled to draw the locking member 180 towards the suture anchoring members 22, 22'. Further drawing the loops 30, 32, 30', 32' can draw the first tissue 12 in close proximity with the second tissue 14 in a desired relationship and subsequently compress the first tissue 12, thereby creating tension in the suture constructs 20, 20'. FIG. 16 illustrates the suture constructs 20, 20' in a tensioned state.

With the first and second tissues 12, 14 in the desired relationship, the tensioning strands 42, 44, 42', 44' can be drawn under tension and attached to a selected area of the second tissue 14 in any suitable manner. For example, the tensioning strands 42, 44, 42', 44' can be attached in a manner substantially similar to that described above for the TFD 10.

Figure 17:
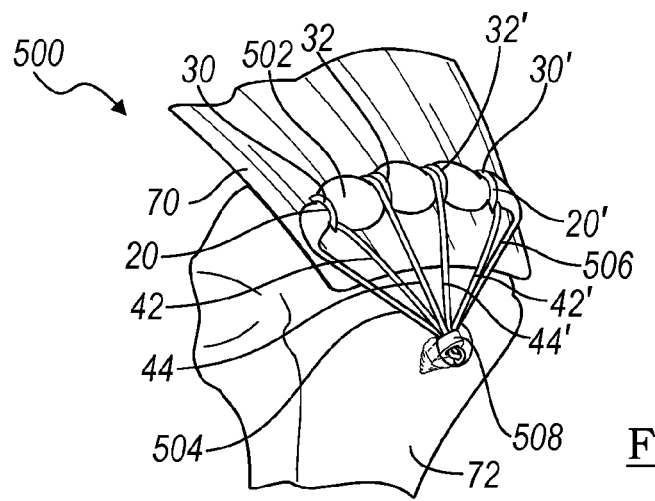
FIG. 17 is a fragmentary environmental perspective view illustrating another exemplary method for affixing a rotator cuff to a humerus using another tissue fixation device according to the present teachings.

With particular reference to FIG. 17, another TFD 500 and surgical method of using the TFD 500 for affixing two tissues according to the present teachings will now be described. The TFD 500 can be used, for example, to affix the rotator cuff 70 to the humerus 72. The TFD 500 and the method illustrate alternate features according to the present teachings including coupling ends of a locking member with a tensioning member of a suture construct. In this way, the locking member can assist the suture construct to resist tension generated in one or both the tissues due to muscle contraction.

For purposes of the example shown in FIG. 17, the TFD 500 can include the self-locking suture constructs 20, 20', the suture anchoring members 22, 22', and a locking member 502. The locking member 502 can be similar to the locking member 24, except that the locking member 502 can have a length sufficient to enable ends 504, 506 to be coupled to the humerus 72 at one or more remote locations. For example, the ends 504, 506 can be coupled at the locations separate from the locations where the locking member 502 is coupled via the suture anchoring members 22, 22'. According to the example shown in FIG. 17, the ends 504, 506 can be coupled to the humerus 72 along with the tensioning strands 42, 44, 42', 44' via a suture anchoring member 508. The ends 504, 506 can be coupled to the suture anchoring member 508 via a knot or other suitable locking device.

With continued reference to FIG. 17, an exemplary method of using the TFD 500 can include coupling the suture constructs 20, 20' to the humerus 72 and passing the loops 30, 32, 30', 32' through the rotator cuff 70 in substantially the same manner as described above for the TFD 10. Next, with the TFD 500 in an untensioned state, the locking member 502 can be passed through and positioned within the loops 30, 32, 30', 32' such that the ends 504, 506 extend past the end loops 30, 30'.

Once the locking member 502 is routed through the loops 30, 32, 30', 32' in the foregoing manner, the tensioning strands 42, 44, 42', 44' can be selectively pulled to cinch the loops 30, 32, 30', 32' around the locking member 502 and to draw the locking member 502 into engagement with the rotator cuff 70. Next, the tensioning strands 42, 44, 42', 44' can be further selectively pulled to draw the locking member 180 towards the suture anchoring members 22, 22'. Further drawing the loops 30, 32, 30', 32' can draw the first tissue 12 in close proximity with the second tissue 14 in a desired relationship and subsequently compress the first tissue 12, thereby creating tension in the suture constructs 20, 20'. FIG. 17 illustrates the suture constructs 20, 20' in a tensioned state. With tension in the suture constructs 20, 20', one or more of the tensioning strands 42, 44, 42', 44' can be cut to remove excess length where the ends of the one or more strands are not to be attached to the humerus 72. Alternately, the tensioning strands 42, 44, 42', 44' can be drawn past an end of the rotator cuff 70 and attached to the humerus 72 as shown. While drawing and/or attaching one or more of the tensioning strands 42, 44, 42', 44', the ends 504, 506 can be drawn past the end of the rotator cuff 70 and attached to the humerus 72.

Figure 18:
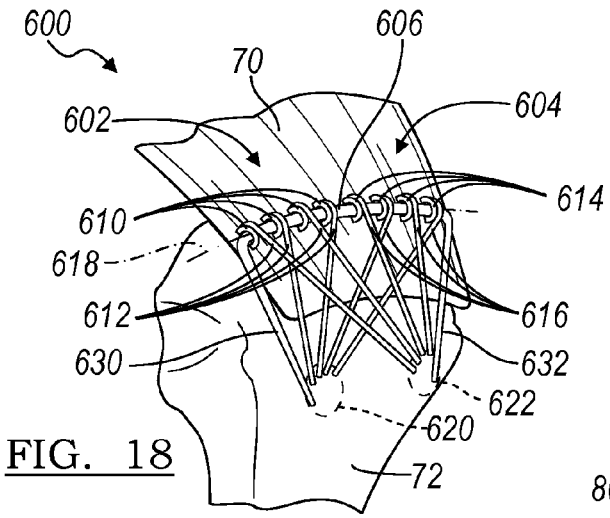
FIG. 18 is a fragmentary environmental perspective view illustrating another exemplary method for affixing a rotator cuff to a humerus using another tissue fixation device according to the present teachings.

With particular reference to FIG. 18, another TFD 600 and surgical method of using the TFD 600 for affixing two tissues according to the present teachings will now be described. The TFD 600 can be used, for example, to affix the rotator cuff 70 to the humerus 72. The TFD 600 and the method illustrate alternate features according to the present teachings including overlapping tensioning members of suture constructs in a criss-cross fashion and securing the tensioning members of each suture construct to the humerus 72 at at least two separate locations. An overlapping structure of the tensioning members can engage and thereby further affix the rotator cuff 70 to the humerus 72. The overlapping structure can further reduce localized stress in one or both the rotator cuff 70 and the humerus 72 by distributing the loads transmitted between the TFD 600 and the rotator cuff 70 and humerus over a larger area and creating a larger area of compression.

According to the example shown in FIG. 18, the TFD 600 can include a first suture construct 602, a second suture construct 604, and a locking member 606. The first and second suture constructs 602, 604 each can include at least two adjustable loops tensioned by corresponding tensioning members. For example, the first suture construct 602 can include four adjustable loops 610 tensioned by four corresponding tensioning strands 612 as shown. Similarly, the second suture construct 604 can include four adjustable loops 614 tensioned by four corresponding tensioning strands 616. The adjustable loops 610, 614 can be created using various suturing techniques and devices. According to the example shown in FIG. 18, the adjustable loops 610, 614 can be created by passing a suture through the rotator cuff 70 using a whip and/or a mattress stitching technique. In various implementations, the adjustable loops 610, 614 can be created from separate sutures attached to the humerus 72 in a manner similar to that discussed below with reference to FIG. 21. The adjustable loops 610, 614 can create a series of loops spaced apart in a substantially linear arrangement along a line or axis 618 as shown. The linear arrangement or axis 618 can extend in a direction substantially transverse to a direction in which the rotator cuff 70 tensions due to muscle contraction.

The tensioning strands 612, 616 can exit the same proximal side of the rotator cuff 70 that the adjustable loops 610, 614 are disposed, and in a substantially linear arrangement in the direction in which the rotator cuff 70 tensions due to muscle contraction. The tensioning strands 612, 614 can exit on either side of the adjustable loops 610, 614. For example, the tensioning strands 610, 614 can each exit in close proximity to the corresponding adjustable loops 610, 614 on a side closest to an end of the rotator cuff 70 as shown. The tensioning strands 612, 616 can be attached to the humerus 72 in at least two selected areas separated in the same direction in which the adjustable loops 610, 614 are arranged.

According to the example shown in FIG. 18, the tensioning strands 612, 616 can be secured at two locations indicated by reference numerals 620, 622. More specifically, at least one of each of the tensioning strands 612 and the tensioning strands 616 can be attached at the first location 620 and at least another one of each of the tensioning strands 612 and the tensioning strands 616 can be attached at the second location 622. For exemplary purposes, the tensioning strands 612, 614 can be attached to the first and second locations 620, 622 in an alternating arrangement as shown. When secured, the tensioning strands 612, 616 secured at the first location 620 can overlap the tensioning strands 612, 616 secured at the second location 622 in a criss-cross fashion. The locking member 606 can extend through each of the loops 610, 614 and can include a first end 630 and a second end 632 that are attached at the first location 620 and the second location 622, respectively.

With continued reference to FIG. 18, an exemplary method of using the TFD 600 will now be described. The method can include creating the loops 610, 614 and tensioning strands 612 and 616 to pass through and exit the rotator cuff 70 and attaching the loops 610, 614 to the humerus 72. The adjustable loops 610 can be attached to the humerus 72 using a first suture anchoring member such as, for example, the suture anchoring member 22 discussed above. Similarly, the adjustable loops 614 can be attached to the humerus 72 using a separate, second suture anchoring member in a similar manner.

Next, with the adjustable loops 610, 614 in an untensioned state, the locking member 606 can be passed through and positioned within the loops 610, 614 such that the ends 630, 632 extend past end loops of the adjustable loops 610, 614. Once the locking member 606 is routed through the loops 610, 614, the tensioning strands 612, 616 can be selectively pulled to cinch the loops 610, 614 around the locking member 606 and to draw the locking member 606 into engagement with the rotator cuff 70. Next, the tensioning strands 612, 616 can be further selectively pulled to draw the locking member 606 towards the humerus 72. Further drawing the loops 30, 32, 30', 32' can draw the rotator cuff 70 in close proximity with the humerus 72 in a desired relationship and subsequently compress the rotator cuff 70 against the humerus 72, thereby creating tension in the loops 610, 614. FIG. 18 illustrates the loops 610, 614 in a tensioned state.

While maintaining the tension in the loops 610, 614, a first pair of the tensioning strands 612 and a first pair of the tensioning strands 616 can be drawn together and attached at the selected location 620. Subsequently, a second pair of the tensioning strands 612 and a second pair of the tensioning strands 616 can be drawn together and attached at the selected location 622. When attached in the foregoing manner, the first and second pairs of the tensioning strands 612, 616 can extend at angles with respect to the axis 618 and overlap in a criss-cross fashion to create an overlapping structure that compresses an end portion of the rotator cuff 70 against the humerus 72. In this way, the overlapping structure can further secure the rotator cuff 70 to the humerus 72.

Figure 19:
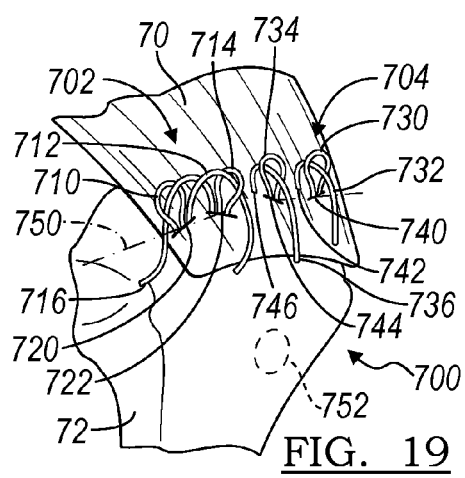
FIG. 19 is a fragmentary environmental perspective view illustrating another exemplary method for affixing a rotator cuff to a humerus using another tissue fixation device according to the present teachings.

With particular reference to FIG. 19, another TFD 700 and surgical method of using the TFD 700 for affixing two tissues according to the present teachings will now be described. The TFD 700 can be used, for example, to affix the rotator cuff 70 to the humerus 72. The TFD 700 and the method illustrate alternate features according to the present teachings including using one or more portions of a suture construct to create a locking member for adjustable loops of the suture construct and securing the portions at a remote location.

According to the example shown in FIG. 19, the TFD 700 can include a first suture construct 702 and a second suture construct 704. The first and second suture constructs 702, 704 can be substantially similar to the suture constructs 20, 20' and can be attached to the humerus 72 in substantially the same way as the suture constructs 20, 20'. The first suture construct 702 can include a first adjustable loop 710 tensioned by a tensioning strand 712 and a second adjustable loop 714 tensioned by a tensioning strand 716. The first adjustable loop 710 and the tensioning strand 712 can pass through a common first aperture 720 formed through the rotator cuff 70 and exit on the same side. The tensioning strand 712 can pass through the second adjustable loop 714. The second adjustable loop 714 and tensioning strand 716 can pass through a common second aperture 722. The tensioning strand 716 can pass through the adjustable loop 710.

The second suture construct 704 can include a third adjustable loop 730 tensioned by a tensioning strand 732 and a fourth adjustable loop 734 tensioned by a tensioning strand 736. The third adjustable loop 730 can pass through a first aperture 740 and the tensioning strand 732 can pass through a separate, second aperture 742 and through the adjustable loop 730. The fourth adjustable loop 734 can pass through a third aperture 744 and the tensioning strand 736 can pass through a separate, fourth aperture 746 and through the fourth adjustable loop 734. The adjustable loops 710, 714, 730, 734 can be spaced apart along a line or axis 750 and the apertures 720, 722, 740, 744 can extend at angles with respect to the axis 750. For example, the apertures 720, 722 can extend at angles of, for example, approximately forty-five degrees (45°) so that the adjustable loops 710, 714 can face each other and to facilitate the passage of the tensioning strands 712, 716. The apertures 740, 744 can extend at angles so that the adjustable loops 730, 734 face towards the apertures 742, 746 and thereby facilitate the passage of the tensioning strands 732, 736. The tensioning strands 712, 716, 732, 736 can be cut to remove excess length and/or attached to a selected area of the humerus 72 at a single, remote location 752 as shown or, alternately, can be secured at two or more remote locations.

With continued reference to FIG. 19, an exemplary method of using the TFD 700 can include attaching the first and second suture constructs 702, 704 to the humerus 72 and passing the adjustable loops 710, 714, 730 through the respective apertures 720, 722 of rotator cuff 70. The method can further include passing the tensioning strands 712, 716, 732 through the respective apertures 720, 722, 734. In various implementations, the tensioning strands 712, 716 can be passed through the apertures 720, 722 at the same time as the respective adjustable loops 710, 714 are passed.

Next, with the first suture construct 702 in an untensioned state, an end of the tensioning strand 712 can be inserted through the second adjustable loop 714 and an end of the tensioning strand 716 can be inserted through the adjustable loop 710. Next, the tensioning strands 712, 714 can be selectively pulled to cinch the adjustable loops 710, 714 around the tensioning strands 712, 714 and engage intermediate portions of the tensioning strands 712, 714 with the rotator cuff 70. Once the tensioning strands 712, 714 are engaged, the tensioning strands 712, 714 can be further selectively pulled to draw the rotator cuff 70 in close proximity to the humerus 72. Once the rotator cuff 70 is positioned against the humerus 72 in a desired relationship, the tensioning strands 712, 714 can be attached to the humerus 72 in tension to retain the relationship.

With the second suture construct 704 in an untensioned state, an end of the tensioning strand 732 can be inserted through the adjustable loop 730 and pulled to cinch the adjustable loop 730 and engage an intermediate portion of the tensioning strand 732 with the rotator cuff 70. Once engaged in the foregoing manner, the tensioning strand 732 can be further pulled to draw the rotator cuff 70 into a desired relationship and subsequently attached in tension to the humerus 72.

Figure 20:
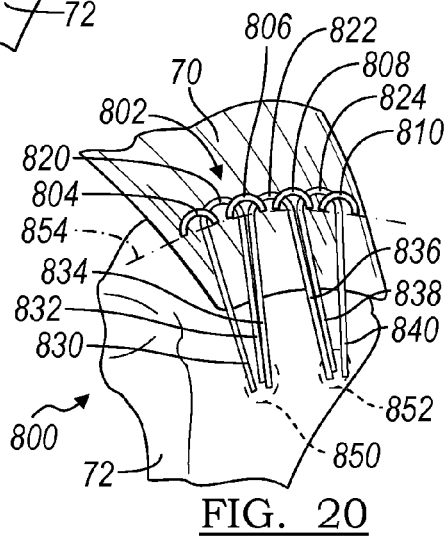
FIG. 20 is a fragmentary environmental perspective view illustrating another exemplary method for affixing a rotator cuff to a humerus using another tissue fixation device according to the present teachings.

With particular reference to FIG. 20, another TFD 800 and surgical method of using the TFD 800 for affixing two tissues according to the present teachings will now be described. The TFD 800 can be used, for example, to affix the rotator cuff 70 to the humerus 72. The TFD 800 can include a suture construct 802 having at least two adjustable loops and at least one locking member that engages the adjustable loops. According to the example shown in FIG. 20, the suture construct 802 can include four adjustable loops 804, 806, 808, 810 and three locking members 820, 822, 824. In various implementations, the adjustable loops 804, 806 and the adjustable loops 808, 810 can be created using the suture construct 20 and the suture construct 20', respectively.

The locking member 820, locking member 822, and locking member 824 can have ends 830, 832, ends 834, 836, and ends 838, 840, respectively. The locking member 820 can extend through and engage the loops 804, 806. The locking member 822 can extend through and engage the loops 806, 808. The locking member 824 can extend through and engage the loops 808, 810. The ends 830, 832, 834 can be attached to a selected area of the humerus 72 at a first location indicated by reference numeral 850, and the ends 836, 838, 840 can be attached at a second location indicated by reference numeral 852.

With continued reference to FIG. 20, an exemplary method of using the TFD 800 can include attaching the loops 804, 806, 808, 810 to the humerus 72 and passing the loops 804, 806, 808, 810 through the rotator cuff 70. The loops 804, 806, 808, 810 can be passed so as to extend along a line or axis 854 and face in a second direction substantially perpendicular to the axis 854. With the loops 804, 806, 808, 810 in an untensioned state, the ends 830, 832, the ends 834, 836, and the ends 838, 840 can be passed through the loops 804, 806, the loops 806, 808, and the loops 808, 810, respectively, in the second direction. When passed in the foregoing manner, portions of the locking members 804, 806, 808, 810 can span the corresponding loops 804, 806, 808, 810. Next, the ends 830, 832, 834, 836, 838, 840 can be pulled to create tension in the loops 804, 806, 808, 810 and to draw the rotator cuff 70 into close proximity with the humerus 72 in a desired relationship. With the rotator cuff 70 and the humerus 72 in the desired relationship, the ends 830, 832, 834, 836, 838, 840 can be attached to the humerus 72 at the respective locations 850, 852 in a tensioned state.

Figure 21:
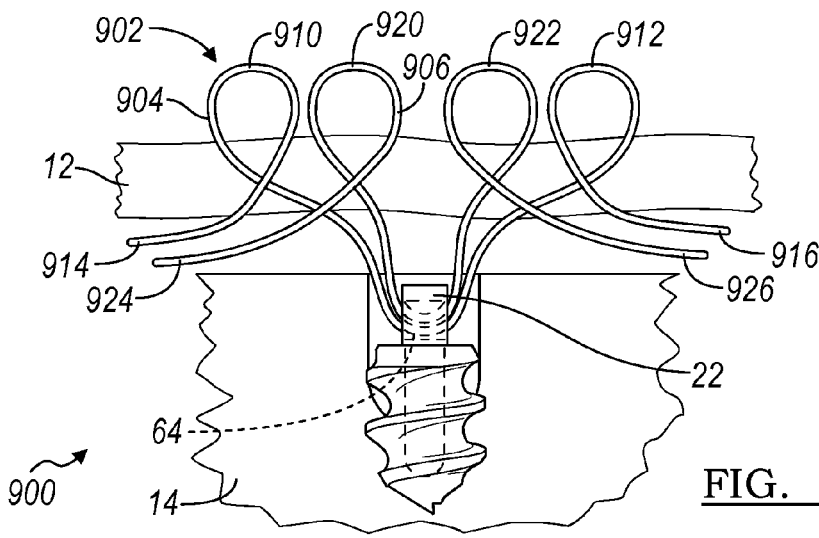
FIG. 21 is an environmental perspective view illustrating another exemplary method for affixing two tissues together using another tissue fixation device according to the present teachings.

With particular reference to FIG. 21, another exemplary TFD 900 and surgical method of using the TFD 900 for affixing the first and second tissues 12, 14 according to the present teachings will now be described. The TFD 900 can be used, for example, to affix the rotator cuff 70 to the humerus 72. The TFD 900 and the method illustrate alternate features according to the present teachings. The alternate features can include engaging a locking member with at least two adjustable loops disposed on one side of a first tissue and drawing the locking member and the first tissue into engagement with a second tissue using tensioning strands disposed between the first and second tissues.

According to the example shown in FIG. 21, the TFD 900 can include a flexible suture construct 902 created by suture strands 904, 906. The suture strand 904 can be passed through the first tissue 12 to create loops 910, 912 that extend from a first side of the first tissue 12 opposite a second side to be engaged with the second tissue 14. The suture strand 904 can be further passed through the first tissue 12 such that ends 914 and 916 exit and extend from the first tissue 12 on the second side of the tissue facing the second tissue 14. The suture strand 906 can be passed through the first tissue 12 to create loops 920, 922 that extend from the first side of the first tissue 12 and ends 924, 926 that exit and extend from the second side of the first tissue 12. Each of the loops 910, 912, 920, 922 can be created by passing the respective suture strands 904, 906 through a single aperture or, alternately, through separate apertures in the first tissue 12. Ends of the suture strands 904, 906 can be secured to the second tissue 14 in any desired manner such as, for example, using one or more suture anchors. While two suture strands 904, 906 forming four loops 910, 912, 920, 922 are shown, fewer or more suture strands can be used where fewer or more loops are desired.

With continued reference to FIG. 21, an exemplary method of using the TFD 900 can include positioning a locking member (not shown) within the loops 910, 912, 920, 922 and subsequently engaging the loops 910, 912, 920, 922 with the first tissue 12 via the locking member. The loops 910, 912, 920, 922 can be engaged by pulling on the ends 914, 916, 924, 926 to cinch the loops 910, 912, 920, 922 into engagement with the locking member and to draw the locking member into engagement with the first tissue 12. The locking member can include one or more features of the locking members 24, 100, 120, 140, 160, 180, 200, 220, 240. With the loops 910, 912, 920, 922 engaged, the ends 914, 916, 924, 926 can be selectively pulled to draw the first tissue 12 into close proximity with the second tissue 14 in a desired relationship. The desired relationship can be maintained by maintaining tension in the loops 910, 912, 920, 922. With the first and second tissues 12, 14 in the desired relationship, the ends 914, 916, 924 and 926 can be drawn and attached to the second tissue 14 in tension to retain the relationship.

Figure 22:
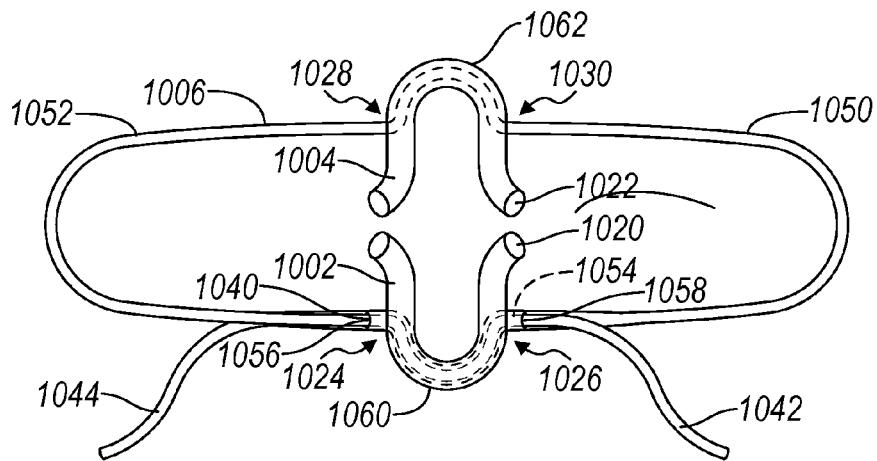
FIG. 22 is a view illustrating a flexible loop construct according to the present teachings.
Figure 23:
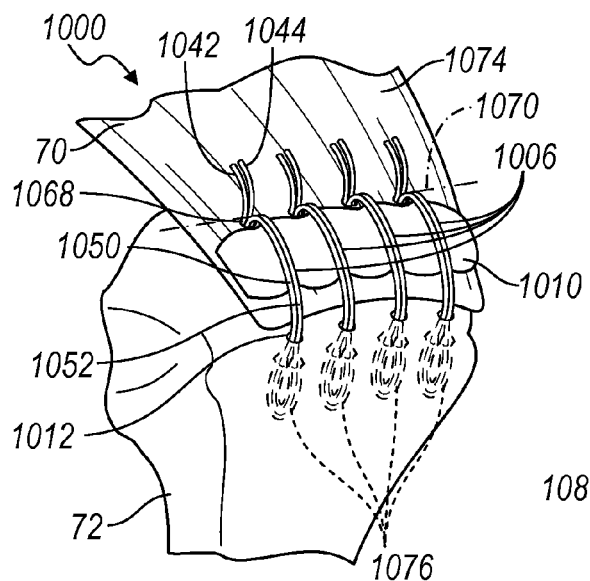
FIGS. 23-24 are fragmentary environmental perspective views illustrating another exemplary tissue fixation device and method of using the tissue fixation device for affixing a rotator cuff to a humerus.
Figure 24:
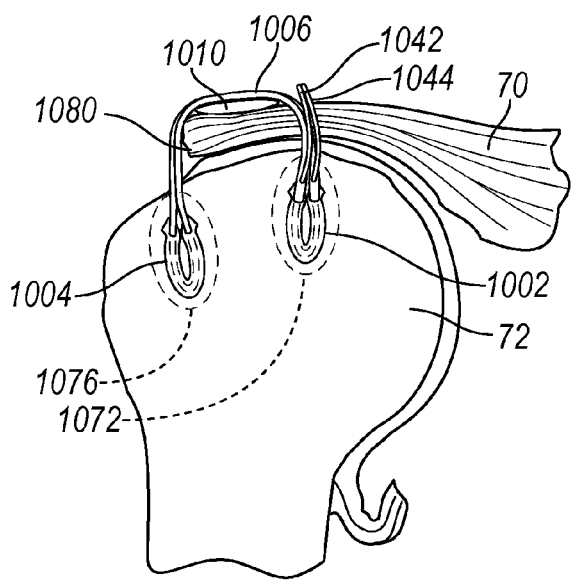

With reference to FIGS. 22-24, another TFD 1000 and surgical method of using the TFD 1000 for affixing the rotator cuff 70 to the humerus 72 according to the present teachings will now be described. The TFD 1000 can include two or more flexible anchors 1002, 1004, one or more self-locking, flexible suture constructs 1006, and a locking member 1010. For example, the TFD 1000 can include four (4) flexible anchors 1002, four (4) flexible anchors 1004, four (4) flexible suture constructs 1006, and one (1) locking member 1010 as shown. The locking member 1010 can incorporate one or more features of the locking members 24, 100, 120, 140, 160, 180, 200, 220, 240 discussed above.

With particular reference to FIG. 22, the flexible anchors 1002, 1004 can be elongate members having a sleeve or tubular construction. The flexible anchors 1002, 1004 can be configured to attach to the humerus 72 within respective bores 1012 formed in the humerus 72. For example, the flexible anchors 1002, 1004 can deform between a first shape configured to be received within the bores 1012 and a second shape larger than the first shape configured to engage the bores 1012. The flexible anchors 1002, 1004 can include longitudinal passages 1020, 1022 and openings 1024, 1026, 1028, 1030 extending through respective walls. The flexible suture construct 1006 can include a braided body 1040 and tensioning strands 1042, 1044 that form a self-locking adjustable loop including loop sections 1050, 1052. The braided body 1040 can define a longitudinal passage 1054 and openings 1056, 1058 in communication with the longitudinal passage 1054. The tensioning strands 1042, 1044 can extend from opposite ends of the braided body 1040.

The loop sections 1050, 1052 can be formed and coupled to the flexible anchors 1002, 1004 by passing the braided body 1040 and the tensioning strand 1042 through the flexible anchors 1002, 1004 as shown. More specifically, the tensioning strand 1042 and the braided body 1040 can pass through the openings 1024, 1026 and the longitudinal passage 1020 of the flexible anchor 1002. The tensioning strand 1042 can further pass through the openings 1028, 1030 and longitudinal passage 1022 of the flexible anchor 1004 and the openings 1056, 1058 and the longitudinal passage 1054 of the braided body 1040. When coupled, the flexible anchor 1002 and the braided body 1040 can be disposed at a first end 1060 and the flexible anchor 1004 can be disposed at a second end 1062. Further details of the flexible anchors 1002, 1004 and the flexible suture construct 1006 are disclosed in commonly assigned U.S. patent application Ser. No. 12/915,962, the entire disclosure of which is expressly incorporated herein by reference.

With continued reference to FIGS. 22-24, the method of using the TFD 1000 can include selectively adjusting a size of the loop sections 1050, 1052 by pulling on the tensioning strand 1042. The size of the loop sections 1050, 1052 can be adjusted to provide a desired length between the first and second ends 1060, 1062. The first ends 1060 can be passed through apertures 1068 in the rotator cuff 70 along a line or axis 1070 and the flexible suture anchors 1002 can secured within the respective bores 1012 formed in the humerus 72 at proximal locations 1072. The proximal locations 1072 can be located beneath the rotator cuff 70 when the rotator cuff 70 is secured in a desired position. The locking member 1010 can be positioned on an outer surface 1074 of the rotator cuff 70 to extend between the flexible suture constructs 1006, and generally parallel to the axis 1070. The second ends 1062 can be drawn over the locking member 1010, past an end 1080 of the rotator cuff 70, and secured within the respective bores 1012 formed in the humerus 72 at distal locations 1076 adjacent the end 1080. The distal locations 1076 can be spaced apart from the proximal locations 1072 and can be disposed adjacent the end 1080 of the rotator cuff 70 as best seen in FIG. 24. When secured, tension in the flexible suture constructs 1006 can compress the locking member 1010. The tensioning strands 1042, 1044 can be cut to a desired length, for example, flush to the outer surface 1074 of the rotator cuff 70.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A tissue fixation apparatus for attaching a first tissue to a second tissue, comprising:
    a flexible construct including: a first adjustable loop and a second adjustable loop which are each configured to pass through the first tissue, and to be spaced apart along an outer surface of the first tissue in a first direction; a first tensioning member extending from the first adjustable loop and pullable to reduce a size of the first adjustable loop; and a second tensioning member extending from the second adjustable loop and pullable to reduce a size of the second adjustable loop;
    an anchor configured to attach the flexible construct to the second tissue in a first selected area of the second tissue; and
    an elongated locking member configured to be received within the first adjustable loop at a first size of the first adjustable loop and to be received within the second adjustable loop at a first size of the second adjustable loop, and to engage the first adjustable loop at a second size of the first adjustable loop size and to engage the second adjustable loop at a second size of the second adjustable loop.

2. The tissue fixation apparatus of claim 1, wherein the locking member includes:
    an adjustable loop member;
    engagement members coupled to the loop member and engageable with the first and second adjustable loops; and
    a tensioning member extending from the adjustable loop member, and configured to reduce a diameter of the adjustable loop member.

3. The tissue fixation apparatus of claim 2, wherein the adjustable loop member includes a filament wound into a coil defining an overall shape of the adjustable loop member.

4. The tissue fixation apparatus of claim 3, wherein the filament passes through the engagement members.

5. The tissue fixation apparatus of claim 2, wherein:
    the locking member further includes a sleeve, the adjustable loop member passes through the sleeve, and the engagement members are disposed adjacent opposite ends of the sleeve.

6. The tissue fixation apparatus of claim 2, wherein the tensioning member is further configured to lock the diameter of the adjustable loop member.

7. The tissue fixation apparatus of claim 1, wherein the locking member includes peripheral recesses configured to receive the first and second adjustable loops.

8. The tissue fixation apparatus of claim 7, wherein the locking member includes barbs defining the peripheral recesses.

9. The tissue fixation apparatus of claim 7, wherein:
    the locking member includes a fabric having first regions adjoining second regions, the first regions having a higher density than the second regions, and the peripheral recesses are disposed adjacent the first regions.

10. The tissue fixation apparatus of claim 1, wherein:
    the flexible construct includes a braided body defining apertures disposed adjacent opposite ends, and the first and second tensioning members extend from the opposite ends and pass through the apertures to create the first and second adjustable loops.

11. The tissue fixation apparatus of claim 10, wherein the braided body and the first and second tensioning members cooperate to lock the first adjustable loop at the second size of the first adjustable loop and the second adjustable loop at the second size of the second adjustable loop.

12. The tissue fixation apparatus of claim 1, wherein the locking member includes:
    a pair of filaments having a length; and
    a braided fabric connecting the filaments along the length, wherein the filaments have diameters larger than a thickness of the braided fabric.

13. The tissue fixation apparatus of claim 1, wherein the locking member includes:
    a braided body defining apertures disposed adjacent opposite ends;
    strands extending from the opposite ends and passing through the apertures to create two adjustable loop members; and
    engagement members attached to the two adjustable loop members, and configured to engage the first and second adjustable loops of the flexible construct.

14. A tissue fixation apparatus for attaching a first tissue to a second tissue, comprising:
    a flexible construct including: a first adjustable loop and a second adjustable loop which are each configured to pass through the first tissue, and to be spaced apart along an outer surface of the first tissue in a first direction, a first tensioning member extending from the first adjustable loop and pullable to reduce a size of the first adjustable loop; and a second tensioning member extending from the second adjustable loop and pullable to reduce a size of the second adjustable loop, wherein the flexible construct is attachable to the second tissue by an anchor; and an elongated locking member configured to be received through the first adjustable loop at a first size of the first adjustable loop and to be received through the second adjustable loop at a first size of the second adjustable loop, and to engage the first adjustable loop at a second size of the first adjustable loop size and to engage the second adjustable loop at a second size of the second adjustable loop.

15. The tissue fixation device of claim 14, wherein the locking member includes:

an adjustable loop member;

engagement members coupled to the adjustable loop member and engageable with the first and second adjustable loops; and a tensioning member extending from the adjustable loop member, and configured to reduce a diameter of the adjustable loop member.

16. The tissue fixation apparatus of claim 15, wherein the adjustable loop member includes a filament wound into a coil defining an overall shape of the adjustable loop member.

17. The tissue fixation apparatus of claim 16, wherein:

the locking member further includes a sleeve, the adjustable loop member passes through the sleeve, and the engagement members are disposed adjacent opposite ends of the sleeve.

18. A tissue fixation apparatus for attaching a first tissue to a second tissue, comprising:

a flexible construct attachable to the second tissue by an anchor, the flexible construct including:

a first adjustable loop and a second adjustable loop which are each configured to pass through the first tissue, and to be spaced apart along an outer surface of the first tissue in a first direction; a first tensioning member extending from the first adjustable loop and pullable to reduce a size of the first adjustable loop; and a second tensioning member extending from the second adjustable loop and pullable to reduce a size of the second adjustable loop; and an elongated locking member configured to be received within the first adjustable loop at a first size of the first adjustable loop and to be received within the second adjustable loop at a first size of the second adjustable loop, the first adjustable loop configured to compress the first tissue between the locking member and the second tissue at a second size of the first adjustable loop, and the second adjustable loop configured to compress the first tissue between the locking member and the second tissue at a second size of the second adjustable loop.

19. The tissue fixation apparatus of claim 18, wherein:

the flexible construct includes a braided body defining apertures disposed adjacent opposite ends, and the first and second tensioning members extend from the opposite ends and pass through the apertures to create the first and second adjustable loops.

20. The tissue fixation apparatus of claim 19, wherein the braided body and the first and second tensioning members cooperate to lock the first and second adjustable loops at the second sizes.

* * * * *